US008784843B2

(12) United States Patent
Belin-Poput et al.

(10) Patent No.: US 8,784,843 B2
(45) Date of Patent: Jul. 22, 2014

(54) STABILIZERS FOR FREEZE-DRIED VACCINES

(75) Inventors: Delphine Magali Belin-Poput, Lyons (FR); Noel Yves Henri Jean Genin, Saint-Genis les Ollieres (FR)

(73) Assignee: Merial Limited, Duluth, GA (US)

( * ) Notice: Subject to any disclaimer, the term of this patent is extended or adjusted under 35 U.S.C. 154(b) by 1849 days.

(21) Appl. No.: 11/522,211

(22) Filed: Sep. 15, 2006

(65) Prior Publication Data

US 2010/0260796 A1 Oct. 14, 2010

Related U.S. Application Data

(60) Provisional application No. 60/717,640, filed on Sep. 16, 2005.

(51) Int. Cl.
*A61K 47/26* (2006.01)
*A61K 39/175* (2006.01)

(52) U.S. Cl.
USPC .................................... 424/278.1; 424/213.1

(58) Field of Classification Search
USPC ........................................... 424/213.1, 278.1
See application file for complete search history.

(56) References Cited

U.S. PATENT DOCUMENTS

| | | | | | |
|---|---|---|---|---|---|
| 3,783,098 | A * | 1/1974 | Calnek et al. | | 435/239 |
| 4,500,512 | A * | 2/1985 | Barme | | 424/218.1 |
| 5,147,756 | A * | 9/1992 | Fodor | | 430/264 |
| 5,869,306 | A * | 2/1999 | Kuma et al. | | 435/440 |
| 5,948,411 | A * | 9/1999 | Koyama et al. | | 424/212.1 |
| 6,051,238 | A | 4/2000 | Volkin et al. | | |
| 6,084,074 | A * | 7/2000 | Kato et al. | | 530/381 |
| 6,159,477 | A * | 12/2000 | Audonnet et al. | | 424/199.1 |
| 2004/0151684 | A1 * | 8/2004 | Mori et al. | | 424/70.14 |
| 2006/0141483 | A1 | 6/2006 | Calton | | |
| 2008/0206281 | A1 | 8/2008 | Look et al. | | |

* cited by examiner

*Primary Examiner* — Shaojia Anna Jiang
*Assistant Examiner* — Jonathan S Lau
(74) *Attorney, Agent, or Firm* — Judy Jarecki-Black; Chad Kitchen; Merial Limited

(57) ABSTRACT

The present invention relates generally to the fields of immunology and vaccine technology. More specifically, the present invention relates to stabilizers for freeze-dried live attenuated immunogenic and/or vaccine compositions, which may comprise, inter alia, canine paramyxovirus. The invention further relates to stabilized, freeze-dried live attenuated immunogenic and/or vaccine compositions of, for example, canine paramyxovirus, which may contain these stabilizers. Other aspects of the invention are described in or are obvious from the following disclosure, and are within the ambit of the invention.

14 Claims, 4 Drawing Sheets

PASTILLE HAVING A REGULAR FORM

MERINGUE ASPECT
Presence of foam into the recipient

SPONGY ASPECT
Pastille having the aspect of a mousse with irregular holes

STUCK ASPECT
Pastille stuck on the bottom after turning over

SPOOLED ASPECT
Pastille having a form of a spool

DEDUPLICATED ASPECT
Separation of the pastille in two parts, following a horizontal plane

Effect of the percentage of non reducing oligosaccharide at T0

CDV titre ($\log_{10}$ CCID50/ml) vs non reducing oligosaccharide (% w/v final concentration)

B.

Effect of the percentage of reducing monosaccharide at T0

CDV titre ($\log_{10}$ CCID50/ml) vs Reducing monosaccharide (% w/v final concentration)

A.

B.

STABILIZERS FOR FREEZE-DRIED VACCINES

CROSS-REFERENCE TO RELATED APPLICATIONS

This application claims priority to U.S. Provisional Application Ser. No. 60/717,640 entitled: "Stabilizers For Freeze-Dried Vaccines", filed Sep. 16, 2006, the disclosure of which is incorporated by reference in its entirety.

Each of these applications, patents, and each document cited in this text, and each of the documents cited in each of these applications, patents, and documents ("application cited documents"), and each document referenced or cited in the application cited documents, either in the text or during the prosecution of the applications and patents thereof, as well as all arguments in support of patentability advanced during prosecution thereof, are hereby incorporated herein by reference.

FIELD OF THE INVENTION

The present invention relates generally to the fields of immunology and vaccine technology. More specifically, the present invention relates to stabilizers for freeze-dried live attenuated immunogenic and/or vaccine compositions that may comprise, inter alia, canine paramyxovirus. The invention further relates to stabilized, freeze-dried live attenuated immunogenic and/or vaccine compositions of, for example, canine paramyxovirus, which may contain these stabilizers. Other aspects of the invention are described in or are obvious from the following disclosure, and are within the ambit of the invention.

BACKGROUND OF THE INVENTION

Immunogenic compositions and vaccine compositions comprising biological ingredients, such as viruses, bacteria, parasites, fungi, proteins, polypeptides, glycoproteins, and especially, attenuated live microorganisms, are markedly sensitive to the conditions by which they are prepared, formulated and stored.

Such biological ingredients can be modified and degraded by chemical reactions (e.g. hydrolysis, deamination, Maillard's reaction), many of which are mediated by water. Liquid water allows for molecular movements and can result in modification of protein conformations in compositions comprising biological ingredients. By limiting access to water or by removing water, a major factor of modification and degradation is reduced. Prior methods to confer stability to biological ingredients have primarily involved freezing the water or removing water by freeze-drying.

Lyophilization, or the process of freeze-drying, is a commonly used technique to remove water in the preparation of dehydrated products. Generally, "freeze-drying" an aqueous composition involves three steps. First, the aqueous composition is frozen under conditions of low temperature. Secondly, the frozen water is removed by sublimation under conditions of reduced pressure and low temperature. At this stage, the composition usually contains about 15% water. Third, the residual water is further removed by desorption under conditions of reduced pressure and higher temperatures. At the end of the lyophilization process, a freeze-dried product, also called a "pastille" or "cake" is produced. The freeze-dried product contains very low residual water (from about 0.5% to about 5% weight/weight) and dry material in an amorphous form. This specific state is qualified as "vitreous".

However, substantial loss of immunogenic activity of biological ingredients are observed during the preparation stages, such as before and during lyophilization, and also during storage of immunogenic compositions and vaccine compositions. The integrity of biological ingredients must be safeguarded to ensure that the immunization efficiency of immunogenic compositions and vaccine compositions is retained. The immunogenic activity of biological ingredients is measured by the ability to induce and stimulate an immunologic response when administered to a host or subject.

To limit the manipulation of subjects and the number of administrations, there is a strong need in the art to provide multivalent immunogenic compositions or vaccine compositions. By definition, a multivalent immunogenic composition or vaccine composition comprises more than one active immunogenic component originating from, or derived from, at least two different pathogens. Viruses from different genera can vary in stability during the freeze-drying step and subsequent storage period, resulting in a loss of viability or infectivity. In the case of viruses such as canine paramyxoviruses, the commonly administered active immunogenic components are live attenuated viruses. To efficiently stimulate the immune system, live attenuated viruses must replicate in the immunized subject. Loss of viability or infectivity can occur during the process of freeze-drying multivalent immunogenic compositions or vaccine compositions, during storage of the compositions, or before administration of the compositions after reconstitution. Thus, stabilizers have been added to such freeze-dried compositions. However, to obtain multivalent immunogenic compositions or vaccine compositions that retain their infectivity and/or viability, a common stabilizer that is able to preserve viability and infectivity of different live attenuated pathogens would be particularly advantageous.

Stabilization of biological ingredients in dry form has typically involved the preservation of antitoxins, antigens and bacteria (Flosodort et al (1935) J. Immunol. 29, 389). However, a limitation in this process included partial denaturation of proteins when dried from an aqueous state at ambient temperatures. Drying from the frozen state helped reduce denaturation and led to better, although incomplete, preservation of biological ingredients including bacteria and viruses (Stamp et al. (1947) J. Gen. Microbiol. 1, 251; Rightsel et al. (1967) Cryobiology 3, 423; Rowe et al. (1971) Cryobiology 8, 251).

More recently, sugars such as sucrose, raffinose and trehalose have been added in various combinations as stabilizers prior to lyophilization of viruses. A large number of compounds have been tested for their ability to stabilize different vaccines containing live attenuated biological ingredients, in particular viruses. Such compounds include SPGA (sucrose, phosphate, glutamate, and albumin; Bovarnick et al. (1950) J. Bacteriol. 59, 509-522; U.S. Pat. No. 4,000,256), bovine or human serum albumin, alkali metal salts of glutamic acid, aluminum salts, sucrose, gelatin, starch, lactose, sorbitol, Tris-EDTA, casein hydrolysate, sodium and potassium lactobionate, and monometallic or dimetallic alkali metal phosphate. Other compounds include, for example, SPG-NZ amine (e.g. U.S. Pat. No. 3,783,098) and polyvinylpyrrolidone (PVP) mixtures (e.g. U.S. Pat. No. 3,915,794).

Vaccine and immunogenic compositions have had a tremendous impact on public health by reducing morbidity and mortality from a variety of virulent pathogens. However, unintended side effects arising from additives in immunogenic compositions and vaccine compositions continue to pose a potential risk that may outweigh any protective and therapeutic attributes of immunogenic compositions and vaccine compositions.

In the form frequently used in vaccines in the United States, gelatin can provoke serious allergic reactions in about 1 out of 2 million doses. Allergic reactions previously thought to result from albumin (egg protein) are more likely caused by gelatin in the same vaccine. In the case of human serum albumin, while no disease has ever been associated with human serum albumin in vaccines, there is a chance of transmission of a virus through this protein, which is derived from human blood.

Bovine-derived products, such as bovine albumin and gelatin, carries the risk of transmission of CJD (Creutzfeld-Jakob disease, also known as "Mad Cow Disease") through beef blood and connective tissue products used in vaccine manufacturing. However, there have been no reported cases where CJD was transmitted through blood or connective tissue products, the prions that cause CJD have not been found in blood or connective tissue, and the use of bovine-derived products from cows imported from countries where there are known cases of Mad Cow Disease is prohibited. Nevertheless, in view of these risks, efforts have been made to eliminate the use of such products in immunogenic compositions that have been observed to elicit unwanted immune effects.

De Rizzo (de Rizzo et al. (1989) Bull. Pan. Am. Health Organ. 23(3), 299-305) reported freeze-dried measles virus preparations containing sorbitol-gelatin or glutamic acid-lactose solutions. These preparations were stored at $-20°$ C. and their viral titers were determined over a 21 month storage period. The resulting data indicated that the freeze-dried viruses without stabilizer are stable when stored at $-20°$ C. over a period of 21 months. Furthermore, it is well known that freeze-dried measles viruses are stable when stored at $-20°$ C. and can retain potency with virtually no loss for many years (Gray A., (1978) Dev. Biol. Stand. 41, 265-266). However, these results were obtained at $-20°$ C. where freeze-dried measles viruses are stable and do not demonstrate an additional stabilizing effect. These results show only that sorbitol-gelatin and glutamic acid-lactose solutions have no negative effect on the stability of the measles viruses that are stored in freeze-dried form at $-20°$ C.

Precausta (Precausta et al (1980) J. Clin. Microbiol. 12(4), 483-489) examined the effects of residual moisture and sealing atmosphere on the infectivity titer of canine distemper virus (CDV) and infectious bronchitis virus (IBV) after freeze-drying. A lactose solution was added to the preparation of CDV to a final concentration of 75 mg/ml, while the IBV vaccine contained 40 mg of mannitol per ml. When CDV titer before freeze-drying was compared to the titer after freeze-drying and after 12 months of storage at 6° C., the CDV titer is decreased from $10^{1.6}$ to $10^{2.0}$ CCID$_{50}$/ml, which reflects a very significant reduction in CDV titer.

These stabilizers often comprise components that are not desirable for administration into a subject, due to safety problems and adverse side effects. Consequently, there is a need for new stabilizers and methods for preserving viability and infectivity of biological ingredients in freeze-dried form, which are safe and suitable for injection to subjects and which have a good aspect.

Citation or identification of any document in this application is not an admission that such document is available as prior art to the present invention.

SUMMARY OF THE INVENTION

The present invention addresses the need in the art by providing, inter alia, new stabilizers for freeze-dried live attenuated immunogenic compositions or vaccine compositions, which may comprise live attenuated canine distemper virus (CDV) and canine parainfluenza type 2 (cPi2). These stabilizers may preserve viability and infectivity of canine paramyxoviruses in addition to other viruses, pathogens, and active immunogenic components, notably during the freeze-drying process and during a long period of storage of the freeze-dried products either at refrigerated temperatures or at room temperature, in particular between from about 4° C. to about 25° C. Importantly, the presently claimed stabilizers for freeze-dried stabilized live attenuated immunogenic compositions or vaccine compositions are safe and suitable for injection to subjects after reconstitution. These freeze-dried stabilized immunogenic compositions may comprise pastilles or cakes a good aspect, i.e., having regular form and uniform color.

The stabilizers of the present invention are advantageously free of ingredients of animal origin, in particular free from serum albumin of human or bovine origin, lactalbumin and gelatin. In this fashion, any potential biological risks of, for example, allergic reactions resulting from gelatin or albumin allergy, such as urticaria and anaphylaxis, and transmission of spongiform encephalitis diseases, notably Creutzfeldt-Jakob disease (CJD) or bovine spongiform encephalitis (BSE; also known as Mad Cow Disease), are minimized or eliminated.

Accordingly, the present invention provides, in one aspect, a stabilizer for a freeze-dried live attenuated canine distemper (CDV) and canine parainfluenza type 2 (cPi2) immunogenic composition or vaccine composition, which may comprise at least one reducing monosaccharide and at least one acid antioxidant compound, wherein the at least one acid antioxidant compound may comprise aspartic acid, glutamic acid, ascorbic acid, or combinations thereof.

In some embodiments, the at least one reducing monosaccharide may comprise glucose, galactose, fructose, mannose, sorbose, or combinations thereof.

In another embodiment, the stabilizer may further comprise at least one bulking agent, which may comprise dextran, maltodextrin, polyvinylpyrrolidone, hydroxyethyl starch, or combinations thereof.

In some embodiments, the stabilizer may further comprise at least one sugar alcohol, which may comprise sorbitol, mannitol, xylitol, maltitol, or combinations thereof.

In another embodiment, the stabilizer may further comprise at least one non-reducing oligosaccharide, which may comprise trehalose, sucrose, raffinose, or combinations thereof.

The present invention also provides stabilizers further comprising at least one sugar alcohol and at least one non-reducing oligosaccharide, wherein the sugar alcohol may comprise sorbitol, mannitol, xylitol, maltitol, or combinations thereof, and wherein the non-reducing oligosaccharide may comprise trehalose, sucrose, raffinose, or combinations thereof.

In another aspect of the present invention, an immunogenic suspension or solution is provided, which may comprise live attenuated paramyxovirus comprising CDV and cPi2, and mixed with the stabilizer of the invention.

One embodiment provides a multivalent immunogenic suspension or solution that may comprise live attenuated paramyxovirus comprising CDV and cPi2, at least one active immunogenic component derived from a pathogen other than a paramyxovirus, and mixed with the stabilizer of the invention. The at least one immunogenic component may be derived from a pathogen comprising Adenoviridae, Parvoviridae, Coronaviridae, Herpesviridae, Poxyiridae, Rhabdoviridae, or combinations thereof.

The at least one active immunogenic component may advantageously comprise live attenuated canine adenovirus type 2 (CAV2) and live attenuated canine parvovirus (CPV).

In some embodiments, the at least one active immunogenic component may comprise a viral vector comprising one or more heterologous immunogens. In other embodiments, the at least one active immunogenic component may comprise a plasmid vector comprising one or more heterologous immunogens.

The immunogenic suspension or solution of the invention provides a stabilizer that may comprise at least one reducing monosaccharide at a final concentration from about 1% to about 5% w/v; from about 1.5% to about 5% w/v; from about 1.5% to about 4% w/v; or from about 2.5% to about 3%.

The immunogenic suspension or solution comprises a stabilizer of the present invention that may comprise at least one acid antioxidant compound at a final concentration from about 0.1% to about 0.3%; from about 0.1% to about 0.25%; or about 0.2% w/v.

The immunogenic suspension or solution comprises a stabilizer that may comprise at least one bulking agent at a final concentration from about 0.5% to about 7.5% w/v; or from about 1.5% to about 5% w/v.

The immunogenic suspension or solution of the present invention comprises a stabilizer, which may comprise at least one sugar alcohol at a final concentration from about 0.5% to about 5% w/v and at least one reducing monosaccharide, with the proviso that the final concentration of the at least one reducing monosaccharide and the at least one sugar alcohol is equal to or less than about 7.5% w/v.

In another embodiment, the immunogenic suspension or solution of the invention comprises a stabilizer is provided, which may comprise at least one non-reducing oligosaccharide from about 0.5% to about 5% w/v final concentration and at least one reducing monosaccharide, with the proviso that the final concentration of the at least one reducing monosaccharide and the at least one non-reducing oligosaccharide is equal to or less than about 7.5% w/v.

Another embodiment of the present invention provides the immunogenic suspension or solution, which may comprise at least one sugar alcohol at a final concentration from about 0.5% to about 5% w/v, at least one non-reducing oligosaccharide at a final concentration from about 0.5% to about 5% w/v, and at least one reducing monosaccharide, with the proviso that the final concentration of the at least one reducing monosaccharide, the at least one sugar alcohol and the at least one non-reducing oligosaccharide is equal to or less than about 12.5% w/v.

The immunogenic suspension or solution of the invention comprises a stabilizer, which may comprise (i) a final concentration of about 1% to about 5% w/v of at least one reducing monosaccharide, and (ii) a final concentration of about 0.1% to about 0.3% w/v of at least one acid antioxidant.

The immunogenic suspension or solution of the invention comprises a stabilizer, which may comprise (i) a final concentration of about 1% to about 5% w/v of a mixture of two reducing monosaccharides, (ii) a final concentration of about 0.1% to about 0.3% w/v of at least one acid antioxidant, and (iii) a final concentration of about 0.5% to about 7.5% w/v of at least one bulking agent.

The immunogenic suspension or solution comprises a stabilizer, which may comprise (i) a final concentration of about 1% to about 5% w/v of at least one reducing monosaccharide, (ii) a final concentration from about 0.5% to about 5% w/v of at least one non-reducing oligosaccharide, (iii) a final concentration from about 0.1% to about 0.3% w/v of at least one acid antioxidant, and (iv) a final concentration from about 0.5% to about 7.5% w/v of at least one bulking agent, with the proviso that the final concentration of (i) and (ii) is equal to or less than about 7.5% w/v.

The immunogenic suspension or solution of the invention comprises a stabilizer, which may comprise (i) a final concentration from about 1.5% to about 4% w/v of at least one reducing monosaccharide, (ii) a final concentration from about 0.5% to about 2.5% w/v of at least one non-reducing oligosaccharide, (iii) a final concentration from about 0.1% to about 0.25% w/v of at least one acid antioxidant, and (iv) a final concentration from about 1.5% to about 5% w/v of at least one bulking agent, with the proviso that the final concentration of (i) and (ii) is equal to or less than about 5% w/v.

In another embodiment, the immunogenic suspension or solution comprises a stabilizer, which may comprise (i) a final concentration from about 1% to about 5% w/v of at least one reducing monosaccharide, (ii) a final concentration from about 0.5% to about 5% w/v of at least one sugar alcohol, (iii) a final concentration from about 0.1% to about 0.3% w/v of at least one acid antioxidant, with the proviso that the final concentration of (i) and (ii) is equal to or less than about 7.5% w/v.

Yet another embodiment of the present invention provides the immunogenic suspension or solution comprising a stabilizer, which may comprise (i) a final concentration from about 1.5% to about 4% w/v of at least one reducing monosaccharide, (ii) a final concentration from about 1.5% to about 3% w/v of at least one sugar alcohol, and (iii) a final concentration from about 0.1% to about 0.25% w/v of at least one acid antioxidant, with the proviso that the final concentration of (i) and (ii) is equal to or less than about 5% w/v.

The immunogenic suspension or solution of the invention comprises a stabilizer, which may comprise (i) a final concentration from about 1% to about 5% w/v of at least one reducing monosaccharide, (ii) a final concentration from about 0.5% to about 5% w/v of at least one sugar alcohol, (iii) a final concentration from about 0.5% to about 5% w/v of at least one non-reducing oligosaccharide, and (iv) a final concentration from about 0.1% to about 0.3% w/v of at least one acid antioxidant, with the proviso that the final concentration of (i), (ii) and (iii) is equal to or less than about 12.5% w/v.

The immunogenic suspension or solution of the present invention comprises a stabilizer, which may comprise (i) a final concentration from about 1.5% to about 4% w/v of at least one reducing monosaccharide, (ii) a final concentration from about 0.5% to about 5% w/v of at least one sugar alcohol, (iii) a final concentration from about 0.5% to about 2.5% w/v of at least one non-reducing oligosaccharide, and (iv) a final concentration from about 0.1% to about 0.25% w/v of at least one acid antioxidant, with the proviso that the final concentration of (i), (ii) and (iii) is equal to or less than about 10% w/v.

Another aspect of the present invention provides a process for freeze-drying a live attenuated CDV and cPi2 immunogenic suspension or solution of the invention, which may comprise (a) contacting the suspension or solution with the stabilizer, thereby forming a stabilized immunogenic suspension or solution; (b) cooling, at atmospheric pressure, the stabilized immunogenic suspension or solution to a temperature of less than about the T'g value of the stabilized immunogenic suspension; (c) drying the stabilized immunogenic suspension or solution by sublimation of ice at low pressure; and (d) removing excess residual water by further reducing pressure and increasing the temperature of the stabilized immunogenic suspension or solution.

In an advantageous embodiment, the temperature in step (b) may be less than about −40° C. The pressure in step (c)

may be less than or equal to about 200 µbar, whereas the pressure in step (d) may be less than or equal to about 100 µbar. The temperature in step (d) may be between about 20° C. to about 30° C.

Another embodiment provides the process of the invention, which may comprise a multivalent immunogenic composition or vaccine composition comprising live attenuated CDV, live attenuated cPi2, and at least one active immunogenic component derived from a pathogen other than a paramyxovirus.

In a further aspect, a freeze-dried stabilized live attenuated CDV and cPi2 immunogenic composition produced by the processes of the invention are provided.

Another aspect provides a freeze-dried stabilized live attenuated CDV and cPi2 immunogenic composition, which may comprise (i) a final concentration from about 20% to about 50% w/w of at least one reducing monosaccharide, (ii) a final concentration of about 1.5% to about 6% w/w of acid antioxidant comprising aspartic acid, glutamic acid, ascorbic acid, or combinations thereof.

A freeze-dried stabilized live attenuated CDV and cPi2 immunogenic composition which may comprise (i) a final concentration from about 20% to about 50% w/w of at least one reducing monosaccharide, (ii) a final concentration from about 2% to about 6% w/w of at least one acid antioxidant comprising aspartic acid, glutamic acid, ascorbic acid, or combinations thereof, and (iii) a final concentration from about 15% to about 70% w/w of at least one bulking agent is also provided by the present invention.

Also provided by the present invention is a freeze-dried stabilized multivalent immunogenic composition or vaccine composition comprising live attenuated CDV, live attenuated cPi2, and at least one active immunogenic component derived from a pathogen other than paramyxovirus produced by the processes of the invention, and which may comprise (i) a final concentration from about 20% to about 50% w/w of at least one reducing monosaccharide, (ii) a final concentration from about 1.5% to about 6% w/w of at least one acid antioxidant comprising aspartic acid, glutamic acid, ascorbic acid, or combinations thereof.

Another aspect of the invention provides a freeze-dried stabilized multivalent immunogenic composition comprising live attenuated CDV, live attenuated cPi2 and at least one active immunogenic component derived from a pathogen other than paramyxovirus, and may comprise (i) a final concentration from about 20% to about 50% w/w of at least one reducing monosaccharide, (ii) a final concentration from about 2% to about 6% w/w of at least one acid antioxidant comprising aspartic acid, glutamic acid, ascorbic acid, or combinations thereof, and (iii) a final concentration from about 15% to about 70% w/w of at least one bulking agent.

In yet another aspect, the invention provides a kit, which may comprise a first vial containing a freeze-dried stabilized immunogenic composition of the invention, and a second vial containing a solvent.

The solvent may be selected from the group consisting of demineralized water, distilled water, water-for-injection, buffer (i.e., phosphate buffer solution), and adjuvant (i.e., water-in-oil emulsions, aluminum hydroxide, carbomers).

These and other embodiments are disclosed or are obvious from and encompassed by the following Detailed Description.

BRIEF DESCRIPTION OF THE DRAWINGS

The following Detailed Description, given by way of example, but not intended to limit the invention to specific embodiments described, may be understood in conjunction with the accompanying Figures, incorporated herein by reference, in which:

FIG. 2 depicts graphs showing the effect of the percentage of (A) non reducing oligosaccharides, and (B) of reducing monosaccharides on the CDV titer, expressed in $\log_{10}$ $CCID_{50}$/ml, at the end of the freeze-drying step (at T0). The final concentration of the non-reducing oligosaccharides and the reducing monosaccharides is expressed as % weight/volume.

DETAILED DESCRIPTION OF THE INVENTION

Figure 1A:
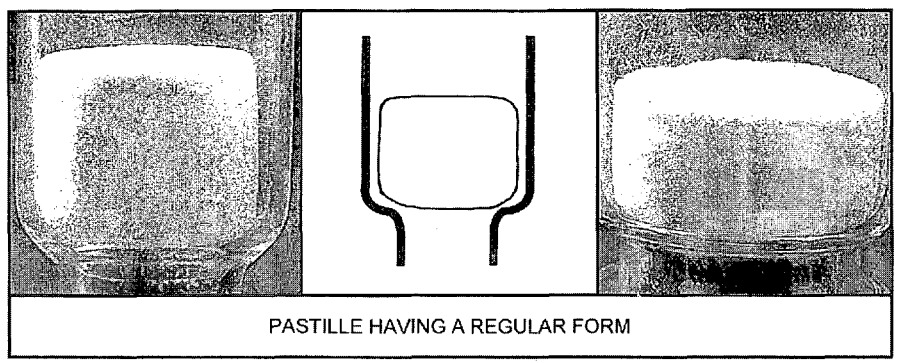
FIG. 1A shows photographs of freeze-dried pastilles having a regular form, a meringue aspect, or a spongy aspect.
Figure 1A:
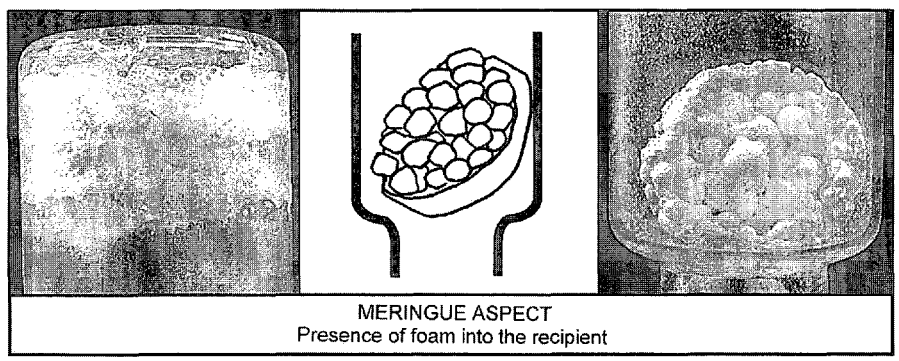
Figure 1A:
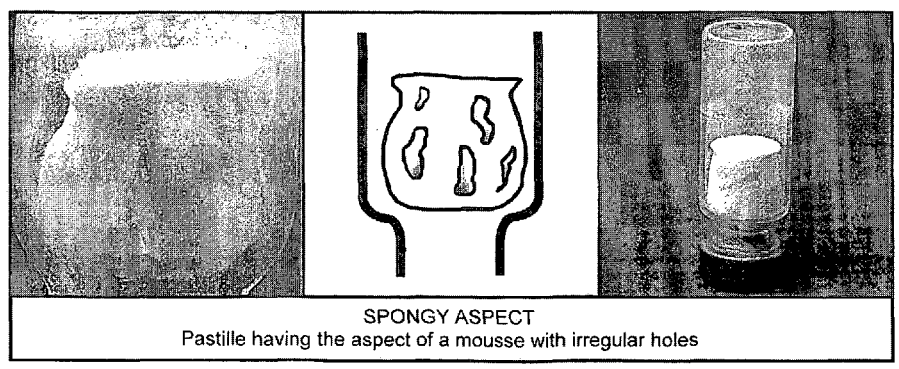

In this disclosure, "comprises," "comprising," "containing" and "having" and the like can have the meaning ascribed to them in U.S. Patent law and can mean "includes," "including," and the like; "consisting essentially of" or "consists essentially" likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

A "subject" in the context of the present invention can be a vertebrate, such as a mammal, bird, reptile, amphibian or fish; more advantageously a human, a companion or domesticated animal; a food-producing or feed-producing animal; livestock, game, racing or sport animal such as, but not limited to, bovines, canines, felines, caprines, ovines, porcines, equines, and avians. Preferably, the vertebrate is a canine.

As used herein, "recombinant" refers to a nucleic acid synthesized or otherwise manipulated in vitro (e.g., "recombinant nucleic acid"), to methods of using recombinant nucleic acids to produce gene products in cells, in subjects, or in other biological systems, or to a polypeptide ("recombinant protein") encoded by a recombinant nucleic acid. "Recombinant means" also encompass the excision and ligation of nucleic acids having various coding regions, domains, or promoter sequences from different sources into an expression cassette or vector for, e.g., inducible or constitutive expression of nucleic acid coding sequences.

As used herein, the term "operably linked" means that the components described are in a relationship permitting them to function in their intended manner.

The term "heterologous" when used with reference to a nucleic acid, indicates that the nucleic acid is in a cell, a virus, a subject, or a bacterium where it is not normally found in nature; or comprises two or more nucleic acid subsequences that are not found in the same relationship to each other as normally found in nature, or is recombinantly engineered so that its level of expression, or physical relationship to other nucleic acids or other molecules in a cell, subject, or structure, is not normally found in nature. For instance, a heterologous nucleic acid can be recombinantly produced having two or more sequences from unrelated genes arranged in a manner not found in nature; e.g., a canine gene operably linked to a promoter sequence inserted into, for example, a poxvirus or adenovirus vector. As an example, a heterologous nucleic acid of interest can encode an immunogenic gene product, wherein the heterologous nucleic acid of interest contained in a vector is administered therapeutically or prophylactically as an immunogenic composition or vaccine composition. Heterologous sequences can comprise various combinations of promoters and sequences, numerous examples of which are described in detail herein.

As used herein, a "vector" is a tool that allows or facilitates the transfer of an entity from one environment to another. By way of example, some vectors used in recombinant nucleic acid techniques allow entities, such as a segment of nucleic acid (such as a heterologous nucleic acid segment, such as a heterologous cDNA segment), to be transferred into a target cell. Also used herein is the term "expression vector". The present invention comprehends recombinant vectors that can include, without limitation, viral vectors, bacterial vectors, fungal vectors, protozoan vectors, plasmid vectors, or recombinants thereof.

With respect to heterologous nucleic acids for expression in a vector (e.g., encoding an epitope of interest and/or an antigen and/or immunogen and/or a therapeutic) and documents providing such heterologous nucleic acids, as well as with respect to the expression of transcription and/or translation factors for enhancing expression of nucleic acid molecules, and as to terms such as "epitope of interest", "therapeutic", "immune response", "immunological response", "protective immune response", "immunological composition", "immunogenic composition", and "vaccine composition", inter alia, reference is made to U.S. Pat. No. 5,990,091 issued Nov. 23, 1999, and WO 98/00166 and WO 99/60164, and the documents cited therein and the documents of record in the prosecution of that patent and those PCT applications; all of which are incorporated herein by reference. Thus, U.S. Pat. No. 5,990,091 and WO 98/00166 and WO 99/60164 and documents cited therein and documents or record in the prosecution of that patent and those PCT applications, and other documents cited herein or otherwise incorporated herein by reference, can be consulted in the practice of this invention; and all heterologous nucleic acid molecules, promoters, and vectors cited therein can be used in the practice of this invention. In this regard, mention is also made of U.S. Pat. Nos. 6,706,693; 6,716,823; 6,348,450; U.S. patent application Ser. Nos. 10/424,409; 10/052,323; 10/116,963; 10/346,021; and WO99/08713, published Feb. 25, 1999, from PCT/US98/16739.

An "antigen" is a substance that is recognized by the immune system and induces an immune response. The antigen may comprise a whole organism, killed, attenuated or live; a subunit or portion of an organism; a recombinant vector containing an insert with immunogenic properties; a nucleic acid piece or fragment capable of inducing an immune response upon presentation to a host animal; a protein, a polypeptide, a peptide, a glycoprotein, an epitope, a hapten, a carbohydrate, a sugar, or any combination thereof. Alternatively, the antigen may comprise a toxin or antitoxin. A similar term used interchangeably in this context is "immunogen". A "pathogen" refers to a specific causative agent of disease, such as a bacterium, fungus, protozoan, parasite, or virus.

As used herein, the terms "immunogenic composition" and "immunological composition" and "immunogenic or immunological composition" cover any composition that elicits an immune response against the antigen or immunogen of interest expressed from vectors; for instance, after administration into a subject, elicits an immune response against the targeted immunogen or antigen of interest. The terms "vaccinal composition" and "vaccine" and "vaccine composition" covers any composition that induces a protective immune response against the antigen of interest, or which efficaciously protects against the antigen; for instance, after administration or injection into the subject, elicits an protective immune response against the targeted antigen or immunogen or provides efficacious protection against the antigen or immunogen expressed from vectors.

As used herein, the term "multivalent" means an immunogenic composition or vaccine composition containing more than one antigen, whether from the same species, from different species, or an immunogenic composition or vaccine composition containing a combination of antigens from different genera.

An "active immunogenic component" in the context of the present invention includes live attenuated pathogens, such as live attenuated viruses, live attenuated bacteria, fungi, or parasites. When the active immunogenic component is part of a multivalent live attenuated CDV and cPi2 immunogenic composition, suspension, or solution of the invention, the active immunogenic component can be advantageously derived from a pathogen other than a paramyxovirus. Also encompassed by the invention are recombinant heterologous immunogens or antigens derived from or originating from one or more pathogens described herein, which can be contained and expressed in, inter alia, viral vectors, bacterial vectors, fungal vectors, and plasmid vectors. The invention also comprehends epitopes of heterologous immunogens or antigens derived from one or more pathogens, immunomodulators such as cytokines, therapeutic agents, toxins, antibodies, antigen-binding fragments of an antibody, adjuvants, or other species such as antisense RNAs, catalytic RNAs, small interfering RNAs, among others.

The term "veterinary composition" means any composition comprising a vector for veterinary use expressing a therapeutic protein as, for example, erythropoietin (EPO) or an immunomodulatory protein, such as, for example, interferon (IFN). Similarly, the term "pharmaceutical composition" means any composition comprising a vector for expressing a therapeutic protein.

The compositions and methods of the present invention can be appropriately applied in the stabilization of immunomodulators such as cytokines, therapeutic agents, toxins, antibodies, antigen-binding fragments of an antibody, adjuvants, or other species such as antisense RNAs, catalytic RNAs, small interfering RNAs, among others. After reconstitution, these compounds may be used for the prevention of diseases as prophylactic immunization or provide relief against symptoms of disease as therapeutic immunization.

The invention encompasses a stabilizer for freeze-dried live attenuated immunogenic compositions comprising at least one reducing monosaccharide and at least one acid antioxidant compound. In some embodiments, the stabilizer can optionally comprise at least one non-reducing oligosaccharide and/or at least one bulking agent and/or at least one sugar alcohol. These stabilizers can preserve or retain the immunogenicity, infectivity, and viability of biological ingredients including, but not limited to, viruses, bacteria, fungi, parasites, proteins, polypeptides, among others. The inventive stabilizers described herein also have a good aspect, i.e. uniform shape and color, and are safe for administration into a subject.

A "reducing monosaccharide" is a saccharide that is able to donate elections, and thus, able to reduce another compound during oxidation-reduction reactions. Generally, a reducing monosaccharide has aldehyde or ketone groups in its structure. Colorimetric tests are available to identify reducing sugars, such as the Fehling's reagent test, which yields a color change from deep blue to red as the copper ion reagent is reduced to the copper metal in presence of a reducing sugar. In the present invention, the reducing monosaccharide preferably comprises glucose, galactose, fructose, mannose, sorbose, or combinations thereof. In one embodiment of the invention, a combination of at least two reducing monosaccharides is provided. The reducing monosaccharides are important for the protection of compositions, notably of proteins and live attenuated pathogens, during the freeze-drying process, particularly during the sublimation step (i.e., first and second dessication steps), wherein the reducing monosaccharides take the place of the sublimated water and maintain cohesion of the biological structure.

Optionally, sugar alcohols and/or non-reducing oligosaccharides can be added to the stabilizer according to the present invention. Combinations of reducing monosaccharides and sugar alcohols, combinations of reducing monosaccharides and non-reducing oligosaccharides, and combinations of reducing monosaccharides, sugar alcohols and non-reducing oligosaccharides are encompassed by the present invention.

Sugar alcohols are chemically alcohols, more precisely polyols, derived from sugar molecules by reduction of the sugar aldehyde group. In the context of the present invention, the sugar alcohols are advantageously monosaccharide alcohols or disaccharide alcohols. The sugar alcohol can advantageously comprise sorbitol, mannitol, xylitol, or maltitol. The stabilizers of the invention can also comprise a mixture of at least two sugar alcohols.

"Non-reducing oligosaccharides" in the context of the invention are sugars comprising from two to ten saccharide units and are unable to reduce another compound during oxidation-reduction reactions. In the present invention, the non-reducing oligosaccharide can be a non-reducing disaccharide or non-reducing trisaccharide, advantageously comprising trehalose, sucrose, or raffinose. The inventive stabilizers can also comprise a mixture of at least two non-reducing oligosaccharides.

The acid antioxidant compound is defined as a chemical compound that reacts with and neutralizes oxidants, free radicals (i.e., molecules with unpaired electrons), or chemicals that release free radicals. In the context of the present invention, the antioxidant compound is in acid form. For purposes of clarity, they are referred to herein as "acid antioxidants". The acid antioxidants can comprise ascorbic acid and/or acidic amino acids, such as aspartic acid and glutamic acid. Advantageously, the acid antioxidant is aspartic acid. The stabilizers preferably do not contain salts of acid antioxidants, e.g. alkali metal salts such as sodium or potassium salts, notably aspartic acid sodium salt, aspartic acid potassium salt, glutamic acid sodium salt, glutamic acid potassium salt, ascorbic acid sodium salt and ascorbic acid potassium salt. Combinations of more than one acid antioxidant compound are also encompassed in the invention.

The bulking agent can be a pharmaceutically or veterinarily acceptable polymer such as but not limited to dextran, maltodextrin, polyvinylpyrrolidone (PVP), crospovidone, and hydroxyethyl starch. Other starch derivatives include, but are not limited to, microcrystalline cellulose, methyl cellulose, carboxy methyl cellulose, hydroxypropylcellulose, hydroxyethyl methyl cellulose, and hydroxypropyl methyl cellulose. Advantageously, the bulking agent can be dextran or PVP, preferably dextran. Also contemplated by the present invention are combinations of at least two bulking agents. The bulking agent increases the T'g value of the immunogenic compositions and vaccine compositions, allowing the use of higher temperatures during freezing. The "T'g value" is defined as the glass transition temperature, which corresponds to the temperature below which the frozen composition becomes vitreous. The bulking agent is primarily responsible for the good aspect observed in the freeze-dried pastilles and cakes of the present invention, notably by retaining the solid form of the pastilles without creating hydrogen bonds.

If dextran is used as a bulking agent, its molecular weight can be from about 5000 Da to about 70000 Da, preferably from about 10,000 Da to about 40,000 Da. If PVP is used as a bulking agent, its molecular weight can be from about 8,000 Da to about 360,000 Da, preferably from about 10,000 Da to about 60,000 Da.

If maltodextrin is used as a bulking agent, its dextrose equivalent value (DE, which is a quantitative measure of the degree of starch polymer hydrolysis) can be from about 3 to about 20, preferably from about 5 to about 18, more preferably from about 10 to about 15. If hydroxyethyl starch is used as a bulking agent, its molecular weight can be from about 70,000 Da to about 450,000 Da, preferably from about 130,000 Da to about 200,000 Da. The degree of substitution of hydroxyethyl starch can be from about 0.4 to about 0.7, preferably from about 0.4 to about 0.6. The degree of substitution is defined as the number of hydroxyethyl group per glucose unit.

Some components in the stabilizer may be not soluble. However, it is well within the purview of the skilled artisan to substitute suitably analogous components (e.g. by selecting a more soluble component) and/or to adapt the amounts or quantities of the insoluble component present in the stabilizer for the purpose of obtaining a soluble stabilizer. The solubility of a component can be easily checked by a visual solubility test. A solubility test comprises the steps of adding all of the components of the stabilizer at a temperature of about 55° C., and mixing for about 30 minutes. After approximately 24 hours at room temperature and without any agitation, the stabilizer can be visually checked for appearance of precipitates. If the stabilizer is transparent or limpid, then all the components of the stabilizer are soluble.

Specific embodiments of the stabilizers of the present invention, named F2, F2B, F6B, F33, F37, A, H, K and U, are described in the Examples herein.

The stabilizers of the present invention can be stored at temperatures from about 10° C. to about 40° C., and preferably from about 15° C. to about 25° C.

Also provided by the invention is a stabilized immunogenic suspension or solution, which comprises an immunogenic suspension or solution comprising a live attenuated virus, such as but not limited to paramyxovirus, mixed with a stabilizer according to the invention. The canine paramyxovirus comprises, among others, canine distemper virus (CDV) and canine parainfluenza type 2 virus (cPi2), both in the form of live attenuated viruses.

An advantageous embodiment of the present invention encompasses live attenuated paramyxoviruses, in particular, canine paramyxoviruses. The canine paramyxovirus is a virus of the Paramyxoviridae family, which includes canine distemper virus (CDV) and canine parainfluenza type 2 virus (cPi2). Canine paramyxoviruses are responsible for a wide variety of diseases in many species of carnivores, in particular domestic animals, such as dogs, or non-domestic animals, such as ferrets, lions, tigers and leopards.

In the stabilized immunogenic suspensions or solutions of the present invention, the final concentration of reducing monosaccharide is from about 1% to about 5% w/v, advantageously from about 1.5% to about 5% w/v, more advantageously from about 1.5% to about 4% w/v, and preferably from about 2.5% to about 3% w/v.

"Final concentration" in the context of the invention means the concentration of a compound in the stabilized immunogenic suspension or solution.

The inventive stabilized immunogenic suspensions or solutions can comprise a final concentration of acid antioxidant compound from about 0.1% to about 0.3% w/v final, particularly from about 0.1% to about 0.25% w/v, and more particularly about 0.2% w/v.

When the stabilized immunogenic suspension or solution comprises at least one bulking agent, the final concentration of bulking agent is from about 0.5% to about 7.5% w/v, and advantageously from about 1.5% to about 5% w/v.

When the stabilized immunogenic suspension or solution comprises at least one reducing monosaccharide and at least one sugar alcohol, the final concentration of reducing monosaccharide is from about 1% to about 5% w/v, advantageously from about 1.5% to about 5% w/v, more advantageously from about 1.5% to about 4% w/v and preferably from about 2.5% to about 3% w/v, the final concentration of sugar alcohol is from about 0.5% to about 5% w/v, and advantageously from about 1.5% to about 3% w/v, with the proviso that the final concentration of the mixture of reducing monosaccharide and sugar alcohol is equal to or less than about 7.5% w/v, and advantageously to about 5% w/v.

When the stabilized immunogenic suspension or solution comprises at least one reducing monosaccharide and at least one non-reducing oligosaccharide, the final concentration of reducing monosaccharide is from about 1% to about 5% w/v, advantageously from about 1.5% to about 5% w/v, more advantageously from about 1.5% to about 4% w/v and preferably from about 2.5% to about 3% w/v, the final concentration of non-reducing oligosaccharide is from about 0.5% to about 5% w/v and advantageously from about 0.5% to about 2.5% w/v, with the proviso that the final concentration of the mixture of reducing monosaccharide and non-reducing oligosaccharide is equal to or less than about 7.5% w/v, and advantageously to about 5% w/v.

When the stabilized immunogenic suspension or solution comprises at least one reducing monosaccharide, at least one non-reducing oligosaccharide and at least one sugar alcohol, the final concentration of reducing monosaccharide is from about 1% to about 5% w/v, advantageously from about 1.5% to about 5% w/v, more advantageously from about 1.5% to about 4% w/v and preferably, from about 2.5% to about 3% w/v; the final concentration of non-reducing oligosaccharide is from about 0.5% to about 5% w/v and advantageously from about 0.5% to about 2.5% w/v, the final concentration of sugar alcohol is from about 0.5% to about 5% w/v, and advantageously from about 1.5% to about 3% w/v, with the proviso that the final concentration of the mixture of reducing monosaccharide, non-reducing oligosaccharide and sugar alcohol is equal to or less than about 12.5% w/v, advantageously about 10% w/v, and more advantageously about 7.5% w/v.

In some embodiments, the stabilizers F2, F2B, F6B, F33, F37, A, H, K or U are mixed with the immunogenic suspensions or solutions or with the multivalent immunogenic suspensions or solutions comprising live attenuated viruses. Preferably, one volume of the F2, F2B, F6B, F33, F37, A, H, K, or U stabilizer is mixed with one volume of the immunogenic suspension or solution comprising live attenuated virus, or with one volume of the multivalent immunogenic suspension or solution comprising live attenuated virus. Their final concentrations in the stabilized suspension or solution are preferably about half the initial concentration.

A live attenuated vaccine or immunogenic composition has the following advantages: it can be administered in low doses, particularly if it is self-replicating; it closely mimics the natural/wild-type infection in a subject, and it provides to the subject all possible immunologically important antigens at the same time, i.e., in a single administration.

It is generally agreed that immunogenic compositions or vaccine compositions based on live attenuated microorganisms have the ability to induce a highly effective type of immune response. Such immunogenic compositions or vaccine compositions have the advantage that, once the animal host has been immunized, entry of the pathogen into the host induces an accelerated recall of earlier, cell-mediated or humoral immunity, which is able to control the further growth of the organism before the infection can assume clinically significant proportions. Immunogenic compositions or vaccine compositions based on a killed pathogen (killed vaccine) are generally conceded in the art to be unable or less likely to achieve this type of response. However, immunogenic compositions or vaccine compositions that contain a live pathogen, depending on the level of attenuation, present the danger that the immunized host, upon immunization, can contract the disease against the protection is being sought. Therefore, immunogenic compositions or vaccine compositions that possess the immunizing attributes of a live pathogen, but that is incapable of causing undesirable side effects upon administration to a subject would be highly desirable.

Live attenuated pathogens can be generated by incorporating a broad range of mutations, including single nucleotide changes, site-specific mutations, insertions, substitutions, deletions, or rearrangements. These mutations may affect a small segment of the pathogen's genome, e.g., 15 to 30 nucleotides, or large segments of the pathogen's genome, e.g., 50 to 1000 nucleotides, depending on the nature of the mutation. For example, mutations can be introduced upstream or downstream of a pathogen's non-coding regulatory region or element to ablate or impair its activity, thereby resulting in an attenuated phenotype.

Mutations of non-coding regulatory regions of the pathogen's genome, which can result in downregulation of replication of a pathogen's gene, and/or downregulation of transcription of a pathogen's gene can result in the production of defective pathogens in each round of replication; i.e. pathogens containing less than the full complement of genomic regions or segments required for a fully infectious pathogen. Therefore, the altered pathogen will demonstrate attenuated characteristics in that the pathogen will give rise to more defective pathogens than wild type pathogens in each round of replication. However, since the amount of protein, antigen, or immunogen synthesized in each round is similar for both wild type pathogen and the defective pathogen, such attenuated pathogens are likely to be capable of inducing a good immune response in a subject.

Where the pathogen's gene encodes a structural protein, e.g., in the case of pathogens such as viruses, a capsid, matrix, surface or envelope protein, the number of particles produced during replication will be reduced such that the mutated pathogen demonstrates attenuated characteristics; e.g., a titer which results in subclinical levels of infection. For example, a decrease in viral capsid expression will reduce the number of nucleocapsids packaged during replication, whereas a decrease in expression of the envelope protein may reduce the number and/or infectivity of progeny virions. Alternatively, a decrease in expression of the viral enzymes required for replication, e.g., the polymerase, replicase, helicase, and the like, should decrease the number of progeny genomes generated during replication. Since the number of infectious particles produced during replication is reduced, the altered viruses demonstrate attenuated characteristics. However, the number of antigenic virus particles produced will generally be sufficient to induce a vigorous immune response in a subject.

An alternative way to engineer attenuated pathogens involves the introduction of an mutation, including, but not limited to, an insertion, deletion or substitution of one or more amino acid residues and/or epitopes into one or more of the pathogen's proteins. This can be readily accomplished by engineering the appropriate mutation into the corresponding gene sequence of the pathogen. Any change that alters the activity of the pathogen's protein so that replication is modified or reduced is encompassed by the present invention.

For example, in the context of attenuated viruses, mutations that interfere with but do not completely abolish viral attachment to host cell receptors and ensuing infection can be engineered into viral surface antigens or viral proteases involved in processing to produce an attenuated strain. Viral surface antigens or virulence factors can be modified to contain insertions, substitution or deletions of one or more amino acids or epitopes that interfere with or reduce the binding affinity of the viral antigen for the host cell receptors. This approach offers an added advantage in that a chimeric virus, which expresses a foreign or heterologous epitope can be produced, which also demonstrates attenuated characteristics. Such viruses are ideal candidates for use as live recombinant vaccines.

Mutations engineered into any of the viral enzymes include, but are not limited to, insertions, deletions and substitutions in the amino acid sequence of the active site of the enzyme. By way of example, the binding site of an enzyme could be altered such that its binding affinity for its substrate is reduced, and as a result, the enzyme is less specific and/or efficient. For example, a target of choice is the viral polymerase complex, since temperature sensitive mutations exist in all polymerase proteins. Therefore, changes introduced into the amino acid positions associated with such temperature sensitivity can be engineered into the viral polymerase gene so that an attenuated viral strain is produced.

CDV is an enveloped single-stranded RNA virus of about 100-300 nm in diameter and belonging to the genus Morbillivirus. The CDV virion core contains a nucleoprotein (NP) peptide that closely associated with viral RNA. A second core peptide is a phosphoprotein (P). The CDV envelope contains three peptides, M protein (matrix protein) and two glycoproteins. The glycoproteins are the hemagglutinin glycoproteins (H) and a fusion (F) glycoprotein. The fusion glycoprotein is degraded into smaller subunits, designated $F_1$ and $F_2$. The H protein is primarily responsible for viral adsorption to target cells and the fusion glycoprotein is responsible for the cell-to-cell fusion. To date, all known distemper virus isolates contain these common viral polypeptides. The route of infection to the dog is by infective aerosol droplets, and transmission of the virus is facilitated by coughing, sneezing and close confinement in a warm, humid, closed environment. Studies suggest that viral infection occurs first in the respiratory epithelium of the upper oronasal tract with subsequent spread to the deep pulmonary parenchyma (Gorham "Canine Distemper", (1960) Advance Veterinary Science, Brandley and Jungher Editors, 6: 288-315).

Tissue macrophages and monocytes located in or along the respiratory epithelium in tonsils appear to be the first cell type to pick up and replicate CDV. The virus then is spread in the bloodstream to distant lymphoreticular tissues. This is accomplished by viremia and occurs anywhere from two to four days after initial infection. Between eight and nine days after infection, the virus spreads beyond lymphoreticular tissues to involve epithelial and mesenchymal tissues (Appel, (1969) Am. J. Vet. Res. 30, 1167-1182). It is at this stage of viral infection that specific host immune responses to viral antigens influence the outcome of disease. The acute fatal form of the disease is characterized by unrestricted viral spread to virtually every tissue in the body. Virus can be found in every excretion and secretion in the infected subject, and by using immunofluorescence methods or antigen tracing techniques, the presence of antigen can be observed in virtually every cell type within the dog. For most of these animals, the most likely cause of death is fulminant fatal neurologic involvement and/or encephalitis.

Some CDV infected dogs exhibit clinically delayed progression of disease and modest convalescent immune responses. Clinical signs, if present, are subtle early in the disease and are a reflection of viral persistence within the central nervous system (CNS). Subsequent development over CNS disease is variable. Most CDV infected dogs exhibit essentially no overt clinical signs of disease and are recognized as convalescent, clinically normal dogs. Actively infected dogs that eventually recover from CDV infection have been shown to demonstrate free circulating anti-viral antibodies on or about post infection day six or seven (Krakowka, et al., (1975) J. Infect. Dis. 132, 384-392). Titers rise rapidly to high levels in early convalescence.

Dogs affected acutely with CDV show variable degrees of depression, anorexia, and fever. The skin may be variably dehydrated, dry-roughened, and inelastic. A proportion of these animals show photophobia and evidence of mucopurulent ocular-nasal discharge. Intermittent diarrhea is a common clinical sign. During this acute viremic phase of the disease, virus is shed in every secretion and excretion. As the disease progresses, pneumonia, frequently due to secondary bacterial invaders, may develop. Dogs in this stage of disease are moderately to severely lymphopenic, depending on the degree or amount of secondary infection. Although acutely affected dogs can show virtually every combination of neurological signs, in its most common presentation, a dog presents petit mal or grand mal seizures. These convulsive episodes occur over time and with increasing frequency.

The second neurologic form of canine distemper is that which occurs with old dog encephalitis (ODE), or occurs after sub-clinical infection and apparent recovery. The CNS signs can be extremely varied in presentation and can be mistaken for brain tumor, head trauma, bacterial meningitis, hydrocephalus, and spinal cord disc disease. A major non-neural manifestation of CDV infection in dogs is CDV-associated immunosuppression (Krakowka, et al., (1980) Am. J. Vet. Res. 41, 284-292). Many of the signs of canine distemper virus infection are attributable to coincidental secondary infectious processes occurring in this debilitated animal.

The disease in dogs can also associated with bacterial pathogens, such as pneumonic bacterial species including, but not limited to, *Bordetella bronchiseptica, Pasteurella* species, *Staphylococcus* and *Streptococcus* species These bacteria are responsible for the purulent conjictivitus, rhinitis, and bronchopneumonia noted clinically in CDV-infected dogs. Mixed viral infections, chiefly of the respiratory type, also are common. In addition to canine adenovirus II infection, reovirus, canine parainfluenza virus, and presumably other viruses such as canine herpes virus, can all be involved in dual or multiple mixed infections.

cPi2 is an RNA virus that induces a respiratory disease that is one of the most commonly encountered viral diseases of the dog. When the combination of parainfluenza virus, canine adenovirus-2 and the bacteria *Bordetella bronchiseptica* occur together, "kennel cough" results. cPi2 also causes tracheobronchitis that, in some animals, results in exudative pneumonia. Signs of cough develop 7 to 9 days after exposure to the virus. The clinical signs are mild and of short duration unless secondary infections occur.

cPi2 is a spherical enveloped virus with an average diameter of 150-200 nm, with a helical nucleocapsid surrounded by a lipid bilayer covered with glycoprotein spikes. Each virus particle contains a single-stranded, nonsegmented, negative-sense RNA genome with nucleoprotein (NP) and phosphoprotein (P) and large (L) proteins. cPi2 infection is acquired through inhalation of infected respiratory droplet nuclei. The nose and the nasopharynx are the primary sites of infection. The virus initiates infection primarily by attaching to the ciliated epithelial cells of these areas through hemagglutinin-neuraminidase proteins, which specifically combine with neuraminic acid receptors in the host cells. Subsequently, the viruses enter the cell via fusion with the cell membrane mediated by F1 and F2 receptors. The viruses multiply and invade other cells both intracellularly and extracellularly. Virus multiplication occurs throughout the tracheobronchiolar tissues, causing enhanced production of mucus.

Laryngotracheitis is an inflammation of larynx and trachea which, when it occurs in dogs, is known commonly as "kennel cough". The main symptom is cough manifested by a short, dry "hack" or by a series of such coughs. At its most severe, the cough may be paroxysmal, and the infection involves the entire respiratory tract, often producing pneumonia. The cough is also characterized as being deep, persistent, non-productive, and generally accompanied by running eyes and nose. The temperature may be normal, although it is generally elevated. The onset of the disease can be sudden and can occur without preliminary signs. Since the disease is very contagious, infected dogs should be isolated to prevent infection of entire populations. The disease produces major economic losses to kennel owners, and while not usually fatal, it may so weaken dogs as to produce serious effects from other diseases.

Live cPi2 virus and other viruses, such as CDV, canine adenovirus Type 2 (CAV2), and canine parvovirus (CPV) can be propagated in animal tissue cultures until both viruses are rendered non-pathogenic, i.e., the viruses are rendered inactive or otherwise attenuated. The cPi2 virus is capable of propagation in a wide variety of tissue culture systems, such as, for example, chick embryo, duck embryo, porcine kidney, porcine testes, embryonic bovine kidney, feline kidney, canine kidney and monkey kidney; and also in established cell lines, such as, for example, Madin Darby bovine kidney (MDBK), Madin Darby canine kidney (MDCK) and Serum Institute rabbit cornea (SIRC).

For the propagation of, for example, canine adenovirus Type 2 (CAV2), kidney tissue cultures are preferred, particularly those derived from bovines and canines, since CAV2 does not favorably replicate in other animal tissue culture systems as does the cPi2 virus. Attenuation of each virus can be accomplished by standard serial passages, including terminal dilution passage techniques, wherein a sufficient number of passages in a susceptible tissue culture can be employed until the virus is rendered non-pathogenic without loss of immunogenicity. An immunogen, immunogenic composition, or immunogenic suspension or solution prepared therefrom can stimulate an immune response in dogs susceptible to disease without producing the clinical symptoms normally due to the virulent agent to any significant degree. The propagation can be conducted in the same or different tissues as those described above.

The passage time intervals should sufficiently allow the virus to replicate between passages, and incubation temperatures are preferably maintained from about 30° C. to about 38° C. The optimum passage time interval depends on the particular culture system and temperature being employed. In any event, whether or not sufficient replication of the virus has occurred can readily be determined by standard techniques such as the hemadsorption technique described in Shelokov, A. (1958) Proc. Soc. Exp. Biol. Med. 97, 802; which is particularly useful for the cPi2 virus, or by cytopathic observations, such as by allowing the virus to grow during a particular passage prior to the point where a gross cytopathic effect can be observed while continuing incubation.

An advantageous method of propagation utilizes canine kidney cells, particularly continuous MDCK cell lines. For example, for immunogenic or vaccine purposes, about at least 15 and preferably from about 20 to about 45 passages from isolation through dog kidney tissue cultures of the viruses can be made at approximately three-day intervals and at incubation temperatures of about 30 to about 38° C. It is preferred to use the higher passage material, since this will benefit the production of favorable immune responses in subjects in need thereof.

In preparing the immunogenic compositions or vaccine compositions, virulent CDV can be grown in cultured mammalian cells in conventional virus growth conditions. The host cells may be seeded with virus at the time of cell planting, or with a CDV-containing media change when the cell monolayer is 90-100% confluent. The multiplicity of infection (MOI) ratio may be from about 0.001 to about 0.05, preferably about 0.01. Any appropriate mammalian cell growth medium, such as, but not limited to, Eagle's Minimum Essential Medium, Dulbecco's Modified Eagle's Medium, Iscove's Modified Dulbecco's Medium, Ham's F12 medium, F15 medium, RPMI 1640 medium, containing animal serum, such as fetal calf serum, calf serum, horse serum, canine serum and the like, at from about 0% to about 10%, supplements such as L-glutamine and other amino acids both essential and non-essential, Hanks Balanced Salt Solution (HBSS), Earle's salt solution, sodium pyruvate, sodium bicarbonate, insulin, transferrin, and antibiotics and antimycotic agents, such as but not limited to, gentamicin, penicillin, streptomycin, polymyxin B, amphotericin, and Fungizone®, can be used to produce the virus or viruses. Also comprehended by the present invention are serum-free cell culture media.

Infected cell cultures maintained in a temperature range of from about 35° C. to about 40° C. for from about 2 to about 7 days post-seeding, at which time virus can be harvested. The infected cultures may be inoculated with cell growth medium, which may be harvested after an additional incubation period of 2 to 5 days. Virus fluids are harvested into sterile containers and may be clarified by filtration. The virus fluids can be further concentrated using conventional ultrafiltration technology (e.g., Millipore Pellicon systems) with filters having particle size exclusion limits of $10^5$ Daltons.

Other live attenuated viruses that can be mixed with the stabilizers of the present invention include, without limitation, Rabies viruses, Influenza viruses, Parainfluenza viruses, Mumps virus, Adenoviruses such as Canine Adenovirus Type 2 (CAV2), Respiratory syncytial virus, Epstein-Barr virus, Rhinoviruses, Poxviruses such as vaccinia virus, swinepox, raccoonpox, avipoxviruses such as fowlpox, canarypox, dovepox, pigeonpox, Polioviruses, Coxsackieviruses, Echoviruses, Coronaviruses, Rubeola virus, Rubella virus, Varicella-zoster virus, Herpes viruses (human and animal), Herpes simplex virus, Parvoviruses such as canine parvovirus (CPV), Cytomegalovirus, Hepatitis viruses such as Canine contagious hepatitis virus, Human papillomavirus, Alphaviruses such as Semliki Forest Virus, Sindbis Virus, Ross River Virus, Eastern equine encephalitis virus, Western equine encephalitis virus, Venezuelan equine encephalitis virus, O'nyong-nyong virus, Flaviviruses such as dengue fever virus and West Nile Virus, Bunyaviruses, Arenaviruses, Rotaviruses, Hepadnaviruses such as Orthohepadnaviruses and Avihepadnaviruses, Filoviruses, Retroviruses such as porcine endogenous retrovirus, HTLV-1, HTLV-2, FeLV, BLV, MLV, MMSV, Mason-Pfizer monkey virus, Lentiviruses such as HIV-1, HIV-2, FIV, SIV, BIV, Feline calicivirus, Feline panleukopenia virus, Feline infectious peritonitis virus, Feline rhinotracheitis virus, TGE virus (swine), and Foot and mouth disease virus.

The immunogenic compositions or suspensions or solutions that comprise, for example, canine paramyxoviruses, are mixed with the stabilizers according to the invention to form stabilized immunogenic suspensions or solutions. Preferably, one volume of the canine paramyxovirus suspension or solution is mixed with one volume of the stabilizer.

The stabilizers of the invention can also be used to stabilize multivalent immunogenic suspensions or solutions, which can comprise, for example, a canine paramyxovirus immunogenic suspension or solution and at least an active immunogenic component originating or derived from a pathogen other than paramyxoviruses. The active immunogenic component as defined herein can comprise live attenuated pathogens, such a live attenuated viruses, bacteria, fungi, or parasites. However, an active immunogenic component can also comprise killed viruses, recombinant heterologous immunogens, antigens, immunogenic subunits (e.g. proteins, polypeptides, peptides, epitopes, haptens) or epitopes of immunogens or antigens derived from or originating from one or more pathogens described herein, which can be expressed from viral vectors, bacterial vectors, plasmid vectors, and the like.

The active immunogenic component of the present invention can comprise one or more immunogens selected from a canine pathogen including, but not limited to, rabies virus, canine adenovirus type 2 (CAV2), canine herpesvirus (CHV), canine parvovirus (CPV), canine coronavirus, *Leptospira canicola, Leptospira icterohaemorragiae, Leptospira grippotyphosa, Borrelia burgdorferi, Bordetella bronchiseptica* and the like, including combinations thereof.

The active immunogenic component can include the HA, F, NP genes from the CDV, the capsid gene from CPV, the spike, M, N genes from Canine coronavirus, the HN and F genes from cPi2, genes from *Leptospira*, genes from *Bordetella*, genes from *Borrelia*, and the gB, gC and gD genes from the canine herpesvirus, among others. These components can be useful as immunogenic compositions or vaccine compositions for protecting canines against disease caused by these pathogens.

Canine Adenovirus Type 2 (CAV2) is widespread and highly contagious to dogs. It produces symptoms resembling a cold. Generally the first signs of the contagious disease are fever, which usually subsides in one to two days. Affected dogs may have tonsillitis, abdominal tenderness, enlarged liver, vomiting and diarrhea. Acute disease is normally fatal. CAV2 may be inactivated or attenuated and combined with the CDV (and/or cPi2) to produce a multivalent vaccine. Alternatively, immunogens or antigens of CAV2, or epitopes of CAV2 immunogens, such as capsid, matrix, or hexon proteins, can be used.

Canine Parvovirus (CPV) is a common intestinal virus which may cause vomiting, diarrhea, gastroenteritis, myocarditis and hepatitis in young dogs. It has been found to be widespread in dogs. CPV can be present in the immunogenic compositions, suspensions, or solutions of the invention as inactivated, live attenuated, or CPV immunogens, antigens, or epitopes of CPV immunogens, such as the VP1, VP2 (capsid) gene products.

Two common bacterial infections of dogs can also be combined in their attenuated form in the stabilized immunogenic compositions, suspensions, or solutions of the present invention; these are *Leptospira canicola* and *Leptospira ichterohaemorrhagiae*. Lepto infections are common in dogs and especially in dogs infected by CDV, cPi2, or combinations of viruses as frequently observed in dogs suffering from distemper or kennel cough, and thus, their inclusions in the stabilized immunogenic compositions, suspensions, or solutions of the present invention are of significant utility.

Other active immunogenic component useful in the compositions and methods of the present invention can comprise one or more immunogens selected from avian pathogens including, but not limited to, *Salmonella typhimurium, Salmonella enteritidis*, Infectious Bronchitis virus (IBV), Newcastle Disease virus (NDV), egg drop syndrome virus (EDS), Infectious Bursal Disease virus (IBDV), turkey virus, avian influenza virus, Marek's disease virus, Herpesviruses such as infectious laryngotracheitis virus, avian infectious bronchitis virus, avian reovirus, poxviruses including avipox, fowlpox, canarypox, pigeonpox, quailpox, and dovepox, avian polyomavirus, avian pneumovirus, avian rhinotracheitis virus, avian reticuloendotheliosis virus, avian retroviruses, avian endogenous virus, avian erythroblastosis virus, avian hepatitis virus, avian anemia virus, avian enteritis virus, Pacheco's disease virus, avian leukemia virus, avian parvovirus, avian rotavirus, avian leukosis virus, avian musculoaponeurotic fibrosarcoma virus, avian myeloblastosis virus, avian myeloblastosis-associated virus, avian myelocytomatosis virus, avian sarcoma virus, avian spleen necrosis virus, and combinations thereof.

As to specific immunogens, the active immunogenic components can also be the HN and F genes of Newcastle Disease Virus, the polyprotein and VP2 genes from infectious Bursal Disease Virus, the S and N genes from Infectious Bronchitis Virus and the gB and gD genes from Marek's Disease Virus. These components can be used as immunogenic compositions or vaccine compositions for protecting avians against disease caused by these pathogens.

Alternatively, the active immunogenic component comprises one or more immunogens from a feline pathogen such as, but not limited to, feline herpesvirus (FHV), feline calicivirus (FCV), feline leukemia virus (FeLV), feline infectious peritonitis virus, feline panleucopenia virus, feline immunodeficiency virus (FIV), rabies virus, and the like, and combinations thereof.

The active immunogenic component can also include the gB, gC and gD genes from the Feline Herpesvirus, the env and gag/pro genes from the FeLV, the env, gag/pol and tat genes from the FIV virus, the capsid gene from the Feline calicivirus, the S modified gene, M, and N gene from the Feline Infectious Peritonitis Virus, and the VP2 gene from the Feline parvovirus. These components can be useful as immunogenic or vaccine compositions for protecting cats against disease caused by these pathogens.

The active immunogenic component can comprise one or more immunogens from an equine pathogen, such as equine herpesvirus (type 1 or type 4), equine influenza virus, equine encephalomyelitis virus (EEV), tetanus, West Nile virus, and the like or combinations thereof.

The active immunogenic component can also include, the gB, gC, gD and Immediate-Early genes from Equine herpesvirus type 1, the gB, gC, gD and Immediate-Early genes from Equine herpesvirus type 4, the HA, NA, M and NP genes from Equine influenza virus, genes from Eastern Equine Encephalitis Virus, genes from Western Equine Encephalitis Virus, genes from Venezuelan Equine Encephalitis Virus, the prM—M-E genes from the West Nile Virus, and genes from Equine arteritis virus, but are not limited to these sequences. These components can be useful as immunogenic compositions or vaccine compositions for protecting horses against disease caused by these pathogens.

The active immunogenic component can comprise one or more immunogens from a bovine pathogen, such as rabies virus, bovine rotavirus, bovine parainfluenza virus type 3 (bCPI2-3), bovine coronavirus, bovine viral diarrhea virus (BVDV), foot and mouth disease virus (FMDV), bovine respiratory syncytial virus (BRSV), Infectious Bovine Rhinotracheitis virus (IBR), *Escherichia coli, Pasteurella multocida, Pasteurella haemolytica*, and the like and combinations thereof.

The active immunogenic component can also be selected from the gB, gC, gD and Immediate-Early genes from Bovine Herpesvirus type 1, the F and G genes from BRSV, the polyprotein, E1, E2 genes from BVDV, the HN and F genes from PI3 virus or genes from Rotavirus. These components can be useful as immunogenic or vaccine compositions for protecting cattle against disease caused by these pathogens.

Further, the active immunogenic component can comprise one or more immunogens from a porcine pathogen such as, but not limited to, swine influenza virus (SIV), porcine circovirus type 2 (PCV-2), porcine reproductive respiratory syndrome virus (PRRSV), pseudorabies virus (PRV), porcine parvovirus (PPV), hog cholera virus (HCV), FMDV, *Mycoplasma hyopneumoniae, Erysipelothrix rhusiopathiae, Pasteurella multocida, Bordetella bronchiseptica, Escherichia coli*, and the like, and combinations thereof.

The active immunogenic component can also include the gB, gC, gD and Immediate-Early genes from PRV, the HA, NA, M and NP genes from Swine influenza virus, the polyprotein, E1, E2 from Hog Cholera Virus, the ORF1 and ORF2 genes from PCV2 virus, the ORF3, ORF4, ORF5, ORF6, or ORF7 from PRRSV virus or genes from *Mycoplasma hyopneumoniae*. These components can be useful as immunogenic compositions or vaccine compositions for protecting pigs against disease caused by these pathogens.

The active immunogenic component can comprise sequences encoding a protein expressed in pathogens such as RNA or DNA viruses like HIV, HCV, HBV, HPV, EBV, HSV, CMV, HTLV, Hanta virus, Ebola virus, Marburg virus, Rift Valley fever virus, Lassa virus and influenza virus, hemorrhagic enteriditis virus (HEV), infectious rhinotracheitis virus (IBRV), among others. Such immunogens can be used advantageously as immunogenic compositions or vaccine compositions to protecting subjects, such as humans, against disease caused by these pathogens.

The active immunogenic component can also be, for example, from any one of the following pathogenic bacteria and their antigens: *Actinobacillus* species such as *Actinobacillus pleuropneumoniae, Bordetella pertussis, Bordetella parapertussis, Bordetella bronchiseptica, Bordetella avium, Chlamydia trachomatis, Chlamydia pneumoniae, Chlamydia psittaci, Klebsiella* species such as *Klebsiella pneumoniae, Mycobacterium tuberculosis, Mycobacterium pseudotuberulosis, Mycobacterium pneumoniae*, Group A *Streptococcus, Streptococcus equi, Streptococcus pneumoniae, Streptococcus agalactiae, Streptococcus pyogenes, Streptococcus viridans, Neisseria gonorrhoeae, Erysipelothrix* species, Enterotoxigenic *Escherichia coli, Vibrio cholerae, Bacillus anthracis, Haemophilus influenzae, Haemophilus somnus, Haemophilus parasuis, Salmonella* species, *Salmonella agona, Salmonella blockley, Salmonella enteriditis, Salmonella hadar, Salmonella Heidelberg, Salmonella montevideo, Salmonella senftenberg, Salmonella cholerasuis, Rickettsia species, Helicobacter pylori, Helicobacter felis, Shigella* species, *Listeria* species, *Legionella pneumoniae, Pseudomonas* species, *Borrelia* species, *Borellia burgdorferi, Neisseria meningitides, Clostridium* species, *Clostridium difficile, Ureaplasma urealyticum, Staphylococcus* species, *Staphylococcus aureus, Enterococcus faecalis, Pasteurella pestis, Campylobacter* species, *Campylobacter jejuni, Treponema* species, *Leptospira* species, *Corynebacterium diphtheria, Hemophilus ducreyi, Hemophilus influenza, Erlichhia* species, among others.

The active immunogenic component may also be derived from a fungus or mold such as *Aspergillus flavus, Aspergillus fumigatis, Penicillium* species, *Fusarium* species, *Candida* species such as *Candida trichophyton, Candida parapsilosis, Candida glabrata, Candida dubliniensis*, and *Candida albicans, Rhizopus species, Cryptococcus* species such as *Cryptococcus neoformans, Cryptococcus grubii, Cryptococcus gattii, Paracoccidiodes brasiliensis, Histoplasma capsulatum*, and other fungi and molds.

The active immunogenic component can also be selected from parasitic antigens derived from parasitic species including, but are not limited to, *Plasmodium* species, *Trypanosome* species, *Giardia* species, *Boophilus* species, *Babesia* species, *Entamoeba* species, *Eimeria* species, *Leishmania* species, *Schistosoma* species, *Brugia* species, *Fascida* species, *Dirofilaria* species, *Wuchereria* species, *Onchocerea* species, *Treponema* species, *Toxoplasma* species, *Cryptococcus* species, *Coccidia* species, *Histomoniasis* species, *Hexamitiasis* species, *Giardia* species, among others; nematodes including *Ascaris* species, *Trichinella* species, and the like, helminthes such as flukes, tapeworms, among others; and other like pathogenic organisms. Methods for preparing immunogens derived from viruses, bacteria, fungi, molds, protozoa, nematodes, and helminthes are known in the art.

Other useful immunogens can be, for example, purified secreted antigen virulence factors, such as toxins, cytotoxins, and the like. Toxin antigens which are detoxified by modifying (toxoids), which can be administered in combination with an adjuvant such as aluminum hydroxide, and can be used to stimulate the formation of toxin-neutralizing antibodies. Examples of toxins that may be used as an immunogen include bacterial endotoxins and exotoxins such as lipopolysaccharide, enterotoxins including heat-labile enterotoxins (LT), heat stable enterotoxins (ST), verotoxin (VT), and the like. Bacterial exotoxin immunogens are secreted into the surrounding medium, and include, for example, diphtheria toxin (*Corynebacterium diphtheriae*), tetanus toxin (*Clostridium tetani*), enterotoxins secreted by *Staphylococcus aureus*, botulinum toxins (*Clostridium botulinum*); and toxins produced by algae such as neurotoxins; and the like. Heat-stable endotoxins, released by autolysis of the bacteria, include, for example, cholera toxins released from the gram negative *Vibrio cholerae*, colicins produced by intestinal bacteria such as *E. coli* (bacteriocin).

Immunogens derived from, or originating from viruses, bacteria, fungi and the like may be produced by in vitro culture methods using appropriate culture medium or host cells lines and conventional methods well known to those of ordinary skill in the art. For example, PRRSV may be cultured in an appropriate cell line, such as MA-104 cell line (see U.S. Pat. Nos. 5,587,164; 5,866,401; 5,840,563; 6,251,404 among others). In a similar manner, PCV-2 may be cultured using PK-15 cells line (see U.S. Pat. No. 6,391,314); SW may be cultured on eggs (U.S. Pat. No. 6,048,537); and *Mycoplasma hyopneumoniae* may be cultured in an appropriate culture medium (U.S. Pat. Nos. 5,968,525; 5,338,543; Ross R. F. et al., (1984) Am. J. Vet. Res. 45: 1899-1905). Advantageously, CDV can be cultured in mink lung cells, such as those described in U.S. Pat. No. 5,178,862. Other techniques for the preparation of virus-derived immunogens are known in the art, and described, for example, in Ulmer et al., Science 259: 1745 (1993); Male et al., Advanced Immunology, pages 14.1-14.15, J.B. Lippincott Co., Philadelphia, Pa. (1989).

Also useful are immunogenic synthetic peptides that mimic antigenic peptide sequences. Such immunogens may be synthesized using a solid-phase technique as described, for example, in R. B. Merrifield, Science 85:2149-2154 (1963), purified, and optionally coupled to a carrier protein such as muramyl dipeptide (MDP), bovine serum albumin (BSA), keyhole limpet hemocyanin (KLH), and the like, using a bifunctional coupling agent such as glutaraldehyde, and the like.

Synthetic antigens are also included within the definition, for example, polyepitopes, flanking epitopes, and other recombinant or synthetically derived antigens. See, e.g., Bergmann et al. (1993) Eur. J. Immunol. 23, 2777-2781; Bergmann et al. (1996) J. Immunol. 157, 3242-3249; Suhrbier, A. (1997) Immunol. Cell Biol. 75, 402-408; Gardner et al. (1998) 12th World AIDS Conference, Geneva, Switzerland, Jun. 28-Jul. 3, 1998. Immunogenic fragments, for purposes of the present invention, can usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the full-length protein sequence, or even a fusion protein comprising two or more, or at least one epitope of the protein.

Accordingly, a minimum structure of a nucleic acid expressing an epitope can comprise nucleotides to encode an epitope, immunogen, or antigen of a protein or polyprotein. A nucleic acid encoding a fragment of the total protein or polyprotein, more advantageously, comprises or consists essentially of or consists of a minimum of about 21 nucleotides, advantageously at least about 42 nucleotides, and preferably at least about 57, about 87 or about 150 consecutive or contiguous nucleotides of the sequence encoding the total protein or polyprotein. Epitope determination procedures, such as, generating overlapping peptide libraries (Hemmer B. et al., (1998) Immunology Today 19(4), 163-168), Pepscan (Geysen et al. (1984) Proc. Natl. Acad. Sci. USA 81, 3998-4002; Geysen et al., (1985) Proc. Nat. Acad. Sci. USA 82, 178-182; Van der Zee R. et al., (1989) Eur. J. Immunol. 19, 43-47; Geysen H. M., (1990) Southeast Asian J. Trop. Med. Public Health 21, 523-533; Multipin® Peptide Synthesis Kits de Chiron) and algorithms (De Groot A. et al., (1999) Nat. Biotechnol. 17, 533-561), and in PCT Application Ser. No. PCT/US2004/022605; all of which are incorporated herein by reference in their entireties can be used in the practice of the invention, without undue experimentation. Other documents cited and incorporated herein may also be consulted for methods for determining epitopes of an immunogen or antigen and thus nucleic acid molecules that encode such epitopes.

In the present invention, the active immunogenic component can also comprise an a therapeutic agent, a cytokine, a toxin, an immunomodulator, a protein, a peptide, an antibody, an antigen-binding fragment of an antibody, an adjuvant, or any other molecule encodable by DNA and desired for delivery to an animal or animal cell or tissue.

Also contemplated by the present invention are the inclusion of antisense, catalytic, or small interfering RNA species in the immunogenic compositions and vaccine compositions of the present invention, which can be targeted against any molecule present within the recipient cell or likely to be present within the recipient cell. These include, but are not limited to RNA species encoding cell regulatory molecules, such as interleukin-6, causative agents of cancer such as human papillomavirus, enzymes, viral RNA and pathogen-derived RNA, such as HIV-1 RNA. The RNAs can also be targeted at non-transcribed DNA sequences, such as promoter or enhancer regions, or to any other molecule present in recipient cells, such as but not limited to, enzymes involved in DNA synthesis or tRNA molecules.

In addition, cytokines and immunomodulators can be co-expressed in the immunogenic compositions and vaccine compositions of the present invention. Examples include, but are not limited to, IL-2, IL-4, TNF-α, GM-CSF, IL-10, IL-12, IGF-1, IFN-α, IFN-β, and IFN-γ.

Specific sequence motifs, such as the RGD motif, may be inserted into the H-I loop of a viral or plasmid vector to enhance its infectivity. This sequence has been shown to be essential for the interaction of certain extracellular matrix and adhesion proteins with a superfamily of cell-surface receptors called integrins. Insertion of the RGD motif may be advantageously useful in immunocompromised subjects. A recombinant vector can be constructed by cloning specific antigen or immunogen or fragments thereof into any of the vectors such as those described herein. The recombinant vector can be used to transduce cells of a vertebrate for use as an immunizing agent. (See, for example, U.S. patent application Ser. No. 10/424,409, incorporated by reference).

Preferably, codons encoding active immunogenic components, such as antigens, immunogens and epitopes, are "optimized" codons, i.e., the codons are those that appear frequently in, i.e., highly expressed canine genes, instead of those codons that are frequently used by, for example, CDV or cPi2. Such codon usage provides for efficient expression of the active immunogenic component in cells. In other embodiments, for example, when the active immunogenic component is expressed in bacteria, yeast or other expression system, the codon usage pattern is altered to represent the codon bias for highly expressed genes in the organism in which the antigen or immunogen is being expressed. Codon usage patterns are known in the literature for highly expressed genes of many species (e.g., Nakamura et al., 1996; Wang et al, 1998; McEwan et al. 1998).

In some cases it may be necessary to modify the coding sequence so that it may be attached to the control sequences with the appropriate orientation; i.e., to maintain the proper reading frame. It may also be desirable to produce mutants or analogs of the desired active immunogenic components. Mutants or analogs may be prepared by the deletion of a portion of a sequence encoding a protein, by insertion of a sequence, and/or by substitution of one or more nucleotides within a sequence. Techniques for modifying nucleotide sequences, such as site-directed mutagenesis, are described in, e.g., Sambrook et al., supra; DNA Cloning, supra; Nucleic Acid Hybridization, supra.

Immunogens useful as active immunogenic components according to the present invention can be contained vectors. Such vectors include, but are not limited to, in vivo recombinant expression vectors such as a nucleic acid vector or a plasmid (EP Application No. 1001025; Chaudhuri P, (2001) Res. Vet. Sci. 70, 255-6), virus vectors such as, but not limited to, adenovirus vectors, poxvirus vectors such as fowlpox (U.S. Pat. Nos. 5,174,993; 5,505,941; and 5,766,599) canarypox vectors (U.S. Pat. No. 5,756,103), retroviral vectors, herpes virus vectors, vectors based on alphavirus, fungal vectors, or bacterial vectors (*Escherichia coli* or *Salmonella* species). Specific examples of vectors useful in the invention are described herein.

The vector can be a viral vector, advantageously an avipox vector containing at least one active immunogenic component, or an epitope thereof, or a fragment thereof. In a particularly advantageous embodiment, the avipox vector is a canarypox vector, advantageously, an attenuated canarypox vector such as ALVAC. Attenuated canarypox viruses are described in U.S. Pat. No. 5,756,103 (ALVAC) and WO01/05934. The avipox vector can be a fowlpox vector, advantageously an attenuated fowlpox vector such as TROVAC. Reference is also made to U.S. Pat. No. 5,766,599 that pertains to the attenuated fowlpox strain TROVAC. In this regard, reference is made to the canarypox available from the ATCC under access number VR-111. Numerous fowlpox virus immunization strains are also available, e.g. the DIFTOSEC CT strain marketed by Merial and the NOBILIS VARIOLE vaccine marketed by Intervet; and, reference is also made to U.S. Pat. No. 5,766,599 which pertains to the attenuated fowlpox strain TROVAC.

A viral vector also useful to deliver active immunogenic components include a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, (1971) Munch. Med. Wschr. 113, 1149-1153; Sutter et al. (1992) Proc. Natl. Acad. Sci. U.S.A. 89, 10847-10851; available as ATCC VR-1508; or NYVAC, see U.S. Pat. No. 5,494,807, for instance, Examples 1 to 6 of U.S. Pat. No. 5,494,807 which discuss the construction of NYVAC, as well as variations of NYVAC with additional ORFs deleted from the Copenhagen strain vaccinia virus genome, as well as the insertion of heterologous nucleic acid coding sequences into sites of this recombinant, and also, the use of matched promoters; see also WO96/40241), an avipox virus or an attenuated avipox virus (e.g., canarypox, fowlpox, dovepox, cowpox, pigeonpox, quailpox, ALVAC or TROVAC; see, e.g., U.S. Pat. Nos. 5,505,941, 5,494,807), swinepox, raccoonpox, camelpox, or myxomatosis virus.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030, inter alia.

When the expression vector is a vaccinia virus, insertion site or sites for the nucleic acid or nucleic acids encoding active immunogenic components such as immunogens, antigens, epitopes and the like, to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al. (1997) Vaccine 15(4), 387-394; Stittelaar K. J. et al. (2000) J. Virol., 2000, 74(9), 4236-4243; Sutter G. et al. (1994) Vaccine 12(11), 1032-1040; and, in this regard it is also noted that the complete MVA genome is described in Antoine G., (1998) Virology 244, 365-396, which enables the skilled artisan to use other insertion sites or other promoters.

Advantageously, the nucleic acid to be expressed can be inserted under the control of a specific poxvirus promoter, e.g., the vaccinia promoter 7.5 kDa (Cochran et al., (1985) J. Virology 54, 30-35), the vaccinia promoter I3L (Riviere et al., (1992) J. Virology 66, 3424-3434), the vaccinia promoter HA (Shida, (1986) Virology 150, 451-457), the vaccinia promoter, 42K (Cooper J. A. et al, (1981) J. Virol. 37(1), 284-94), the cowpox promoter ATI (Funahashi et al (1988) J. Gen. Virol. 69, 35-47), the vaccinia 11K promoter (U.S. Pat. No. 5,017,487); the vaccinia promoter H6 (Taylor J. et al., (1988) Vaccine 6, 504-508; Guo P. et al. (1989) J. Virol. 63, 4189-4198; Perkus M. et al. (1989) J. Virol. 63, 3829-3836), or synthetic vaccinia or poxyiral promoters, inter alia.

Advantageously, for the immunization of mammals, the expression vector can be a canarypox or a fowlpox vector. In this way, there can be expression of the heterologous proteins with limited or no productive replication.

Another viral vector useful to deliver and express active immunogenic components is adenovirus. Adenovirus is a non-enveloped DNA virus. Vectors derived from adenoviruses have a number of features that make them particularly useful for gene transfer. A recombinant adenovirus vector is an adenovirus vector that carries one or more heterologous nucleotide sequences (e.g., two, three, four, five or more heterologous nucleotide sequences). For example, the biology of the adenoviruses is characterized in detail, the virus is extremely efficient in introducing its DNA into the host cell, the virus can infect a wide variety of cells and has a broad host range, the virus can be produced in large quantities with relative ease, and the virus can be rendered replication defective by deletions in the early region 1 ("E1") of the viral genome.

In contrast to, for example, retroviruses, adenoviruses do not integrate into the host cell's genome, are able to infect non-dividing cells, and are able to efficiently transfer recombinant genes in vivo (Brody et al., 1994). These features make adenoviruses attractive candidates for in vivo gene transfer of, for example, a heterologous nucleic acid of interest into cells, tissues or subjects in need thereof.

Adenovirus vectors containing multiple deletions are preferred to both increase the carrying capacity of the vector and reduce the likelihood of recombination to generate replication competent adenovirus (RCA). Where the adenovirus contains multiple deletions, it is not necessary that each of the deletions, if present alone, would result in a replication defective adenovirus. As long as one of the deletions renders the adenovirus replication defective, the additional deletions may be included for other purposes, e.g., to increase the carrying capacity of the adenovirus genome for heterologous nucleotide sequences. Preferably, more than one of the deletions prevents the expression of a functional protein and renders the adenovirus replication defective. More preferably, all of the deletions are deletions that would render the adenovirus replication defective.

Embodiments of the invention employing adenovirus recombinants may include E1-defective or deleted, E3-defective or deleted, and/or E4-defective or deleted adenovirus vectors, or the "gutless" adenovirus vector in which all viral genes are deleted. The adenovirus vectors can comprise mutations in E1, E3, or E4 genes, or deletions in these or all adenoviral genes. The E1 mutation raises the safety margin of the vector because E1-defective adenovirus mutants are said to be replication-defective in non-permissive cells, and are, at the very least, highly attenuated. The E3 mutation enhances the immunogenicity of the antigen by disrupting the mechanism whereby adenovirus down-regulates MHC class I molecules. The E4 mutation reduces the immunogenicity of the adenovirus vector by suppressing the late gene expression, thus may allow repeated re-immunization utilizing the same vector. The present invention comprehends adenovirus vectors of any serotype or serogroup that are deleted or mutated in E1, E3, E4, E1 and E3, and E1 and E4.

A "gutless" adenovirus vector is the latest model in the adenovirus vector family and is derived from human adenovirus sequences. Its replication requires a helper virus and a special human 293 cell line expressing both E1a and Cre, a condition that does not exist in natural environment; the vector is deprived of all viral genes, thus the vector as a vaccine carrier is non-immunogenic and may be inoculated multiple times for reimmunization. The "gutless" adenovirus vector also contains 36 kb space for accommodating heterologous nucleic acid(s) of interest, thus allowing co-delivery of a large number of antigen or immunogens into cells.

Thus, the vector in the invention can be any suitable recombinant virus or virus vector, including, without limitation, a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, (as in documents incorporated herein by reference); or the vector can be a plasmid. The herein cited and incorporated herein by reference documents, in addition to providing examples of vectors useful in the practice of the invention, can also provide sources for other active immunogenic components to be expressed by vector or vectors in, or included in, the stabilized immunogenic compositions, suspensions, or solutions of the invention.

Elements for the expression of the active immunogenic components can advantageously be present in a plasmid vector. The term plasmid covers any DNA transcription unit comprising a nucleic acid according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

In a minimum manner, expression of an active immunogenic component, such as an antigen, an immunogen, and an epitope, comprises an initiation codon (ATG), a stop codon and a promoter, and optionally also a polyadenylation sequence for certain vectors such as plasmid and certain viral vectors, e.g., viral vectors other than poxviruses. When the nucleic acid encodes a polyprotein fragment in the vector, an ATG is placed at the 5' terminus of the reading frame and a stop codon is placed at the 3' terminus. Other elements for controlling expression may be present, such as enhancer sequences, stabilizing sequences and signal sequences permitting the expression, modification, and secretion of the protein.

A nucleic acid "coding sequence" or a "nucleotide sequence encoding" a particular protein is a DNA sequence which is transcribed and translated into a polypeptide in vitro or in vivo when placed under the control of appropriate regulatory elements. The boundaries of the coding sequence are determined by a start codon at the 5' terminus and a translation stop codon at the 3' terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

Nucleic acid "control elements" refer collectively to promoters, RNA splice sites, ribosome binding sites, polyadenylation signals (e.g., polyadenylation signals derived from bovine growth hormone, SV40 polyadenylation signal), transcription termination sequences, upstream regulatory domains, enhancers, origins of replication (which can be bacterial origins, e.g., derived from bacterial vectors such as pBR322, or eukaryotic origins, e.g., autonomously replicating sequences (ARS)), packaging signals, leader sequences that may or may not be contained in the coding sequence of an active immunogenic component, such as an immunogen, antigen or epitope. If a signal sequence is included, it can either be the native, homologous sequence, or a heterologous sequence. Leader sequences can be removed by the host in post-translational processing. See, e.g., U.S. Pat. Nos. 4,431,739; 4,425,437; 4,338,397, and the like, which collectively provide for the transcription and translation of a coding sequence in a host cell.

Not all of these control sequences need always be present in a recombinant vector so long as the desired gene is capable of being transcribed and translated. A control element, such as a promoter "directs the transcription" of a coding sequence in a cell when RNA polymerase binds to the promoter and transcribes the coding sequence into mRNA. The resultant mRNA is subsequently translated into the polypeptide encoded by the coding sequence.

A variety of promoter/enhancer elements may be used depending on the level and tissue-specific expression desired. The promoter can be constitutive or inducible (e.g., the metallothionein promoter, the tetracycline inducible promoter, and the ecdysone inducible promoter, among others), depending on the pattern of expression desired. The promoter may be native or heterologous and can be a natural or a synthetic sequence. "Heterologous" in this context describes a transcriptional initiation region that is not found in the wild-type host into which the transcriptional initiation region is introduced. The promoter is chosen so that it will function in the target cell(s) or tissue(s) of interest. Brain-specific, hepatic-specific, and muscle-specific (including skeletal, cardiac, smooth, and/or diaphragm-specific) promoters are contemplated by the present invention. Mammalian and avian promoters are also preferred, particularly canine promoters.

The promoter can advantageously be an "early" promoter. An "early" promoter is known in the art and is defined as a promoter that drives expression of a gene that is rapidly and transiently expressed in the absence of de novo protein synthesis. The promoter can also be a "strong" or "weak" promoter. The terms "strong promoter" and "weak promoter" are known in the art and can be defined by the relative frequency of transcription initiation (times per minute) at the promoter. A "strong" or "weak" promoter can also be defined by its affinity to RNA polymerase.

The heterologous gene can be placed under the control of a promoter, ribosome binding site (for bacterial expression) and, optionally, an enhancer or operator, so that the DNA sequence encoding the desired protein is transcribed into RNA in a host cell or subject transformed by a vector containing the active immunogenic component.

Control elements and other regulatory sequences may be ligated to the coding sequence prior to insertion into a vector, such as the cloning vectors described above. Alternatively, the coding sequence can be cloned directly into an expression vector that already contains the control sequences and an appropriate restriction site.

More preferably, the antigens or immunogens are operatively associated with, for example, a human cytomegalovirus (CMV) major immediate-early promoter, a simian virus 40 (SV40) promoter, a β-actin promoter, an albumin promoter, an Elongation Factor 1-α (EF1-α) promoter, a PγK promoter, a MFG promoter, or a Rous sarcoma virus promoter. Other expression control sequences include promoters derived from immunoglobin genes, adenovirus, bovine papilloma virus, herpes virus, and so forth. Any mammalian viral promoter can also be used in the practice of the invention, in addition to any canine viral promoter. Among canine promoters of viral origin, the promoters of immediate early genes of the infectious canine herpes virus, early (i.e., thymidine kinase, DNA helicase, ribonucleotide reductase) or late promoters, can be used in the methods and vectors of the present invention. Other promoters include the E1 promoter of canine adenovirus, as well as the canine major histocompatibility complex I promoter. Moreover, it is well within the purview of the skilled artisan to select a suitable promoter that expresses the antigen or immunogen of interest at sufficiently high levels so as to induce or elicit an immunogenic response to the antigen or immunogen, without undue experimentation.

It has been speculated that driving heterologous nucleotide transcription with the CMV promoter can result in downregulation of expression in immunocompetent animals (see, e.g., Guo et al., 1996). Accordingly, it is also preferred to operably associate the antigen or immunogen sequences with, for example, a modified CMV promoter that does not result in this downregulation of antigen or immunogen expression.

The vectors of the invention can also comprise a polylinker or multiple cloning site ("MCS"), which can advantageously be located downstream of a promoter. The polylinker provides a site for insertion of the antigen or immunogen molecules that are "in-frame" with the promoter sequence, resulting in "operably linking" the promoter sequence to the antigen or immunogen of interest. Multiple cloning sites and polylinkers are well known to those skilled in the art.

The vectors described herein can also comprise antibiotic resistance genes. Examples of such antibiotic resistance genes that can be incorporated into the vectors of the invention include, but are not limited to, ampicillin, tetracycline, neomycin, zeocin, kanamycin, bleomycin, hygromycin, chloramphenicol, among others.

In embodiments where there is more than one antigen or immunogen, the antigen or immunogen sequences may be operatively associated with a single upstream promoter and one or more downstream internal ribosome entry site (IRES) sequences (e.g., the picornavirus EMC IRES sequence). An IRES sequence allows for multicistronic translation of two or more coding sequences from a single mRNA sequence.

The vectors of the invention can then be used to transform an appropriate host cell or subject. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, Madin-Darby canine kidney ("MDCK") cells, as well as others. Similarly, bacterial hosts such as *E. coli, Bacillus subtilis, Salmonella* spp., *Shigella* spp., and *Streptococcus* spp., will find use in the present invention. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect hosts useful in the present invention include, but are not limited to, *Spodoptera frugiperda* cells.

Alternatively, the vectors can be used to infect a cell in culture to express a desired gene product, e.g., to produce a protein or peptide of interest. Preferably, the protein or peptide is secreted into the medium and can be purified therefrom using routine techniques known in the art. Signal peptide sequences that direct extracellular secretion of proteins are known in the art and nucleotide sequences encoding the same can be operably linked to the nucleotide sequence encoding the peptide or protein of interest by routine techniques known in the art. Alternatively, the cells can be lysed and the expressed recombinant protein can be purified from the cell lysate. Preferably, the cell is a vertebrate cell, more preferably a mammalian cell.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; W091/11525; WO 94/16716; WO 96/39491; WO 98/33510; EP 265785; EP 0 370 573; Andreansky et al. (1996) Proc. Natl. Acad. Sci. USA 93, 11313-11318; Ballay et al. (1993) EMBO J. 4, 3861-65; Felgner et al. (1994) J. Biol. Chem. 269, 2550-2561; Frolov et al. (1996) Proc. Natl. Acad. Sci. USA 93, 11371-11377; Graham, F. L. (1990) Trends Biotechnol. 8, 85-87; Grunhaus et al. (1992) Sem. Virol. 3, 237-52; Ju et al. (1998) Diabetologia 41, 736-739; Kitson et al. (1991) J. Virol. 65, 3068-3075; McClements et al. (1996) Proc. Natl. Acad. Sci. USA 93, 11414-11420; Moss, B. (1996) Proc. Natl. Acad. Sci. USA 93, 11341-11348; Paoletti, E. (1996) Proc. Natl. Acad. Sci. USA 93, 11349-11353; Pennock et al. (1984) Mol. Cell. Biol. 4, 399-406; Richardson (Ed), (1995) Methods in Molecular Biology 39, "Baculovirus Expression Protocols," Humana Press Inc.; Smith et al. (1983) Mol. Cell. Biol. 3, 2156-2165; Robertson et al. (1996) Proc. Natl. Acad. Sci. USA 93, 11334-11340; Robinson et al. (1997) Sem. Immunol. 9, 271; and Roizman, B. (1996) Proc. Natl. Acad. Sci. USA 93, 11307-11312.

Expression in the subject of the heterologous sequence can result in an immune response in the subject to the expression products of the antigen or immunogen. Thus, the active immunogenic components of the present invention may be used in an immunogenic composition or vaccine composition to provide a means to induce an immune response, which may, but need not be, protective. The molecular biology techniques used in the context of the invention are described by Sambrook et al. (2001).

Even further alternatively or additionally, in the immunogenic or vaccine compositions encompassed by the present invention, the nucleotide sequence encoding the antigens or immunogens can have deleted therefrom a portion encoding a transmembrane domain. Yet even further alternatively or additionally, the vector or immunogenic composition can further contain and express in a host cell a nucleotide sequence encoding a heterologous tPA signal sequence such as a mammalian tPA and/or a stabilizing intron, such as intron II of the rabbit β-globin gene.

A vector can be administered to a subject in an amount to achieve the amounts stated for gene product (e.g., epitope, antigen, therapeutic, and/or antibody) compositions. The invention envisages dosages below and above those exemplified herein, and for any composition to be administered to a subject, including the components thereof, and for any particular method of administration, it is preferred to determine toxicity, such as by determining the median cell culture infective dose ($CCID_{50}$), the lethal dose (LD) and $LD_{50}$ in a suitable subject; and the dosage of the composition, concentration of components therein and timing of administering the composition, which elicit a suitable response, such as by titrations of sera and analysis thereof, e.g., by ELISA and/or seroneutralization analysis. Such determinations do not require undue experimentation from the knowledge of the skilled artisan, this disclosure and the documents cited herein.

Multivalent immunogenic compositions and/or vaccine compositions and/or immunogenic suspensions or solutions comprising live attenuated CAV2, live attenuated CDV, live attenuated cPi2, and live attenuated CPV, and comprising a stabilizer according to the present invention have been tested in the Examples herein. These multivalent vaccines showed good stability for CDV, cPi2, CAV2 and CPV. This demonstrates that the stabilizers of the present invention are able to preserve viability and infectivity of CDV, cPi2, CAV2 and CPV. This also demonstrates that the stabilizers of the present invention are able to preserve viability and infectivity of a variety of viruses other than canine paramyxoviruses, notably of canine parvovirus and canine adenovirus. The stabilizers according to the present invention can be also used as a monovalent immunogenic composition or vaccine composition comprising CAV, CPV, CDV or cPi2.

Preferably one volume of the multivalent suspension or solution (i.e. canine paramyxovirus and at least one active immunogenic component derived from a pathogen other than paramyxoviruses) is mixed with one volume of the stabilizer.

Also provided by the invention is a process for producing a freeze-dried stabilized live attenuated immunogenic composition or vaccine composition comprising, for example, canine paramyxoviruses, which comprises the step of lyophilizing a stabilized suspension or solution formed by a live attenuated canine paramyxovirus suspension or solution, mixed with a stabilizer according to the invention.

Another aspect of the present invention is a process for producing a freeze-dried stabilized multivalent immunogenic composition or vaccine composition, which comprises the step of lyophilizing a stabilized multivalent suspension or solution comprising, for example, a live attenuated canine paramyxovirus suspension or solution and at least one active immunogenic component derived from a pathogen other than paramyxovirus, mixed with a stabilizer according to the invention.

"Freeze-drying" involves lyophilization and refers to the process by which a suspension is frozen, after which the water is removed by sublimation at low pressure. As used herein, the term "sublimation" refers to a change in the physical properties of a composition, wherein the composition changes directly from a solid state to a gaseous state without becoming a liquid. As used herein, the "T'g value" is defined as the glass transition temperature, which corresponds to the temperature below which the frozen composition becomes vitreous.

A process for freeze-drying an immunogenic suspension or solution according to the invention can comprise the steps of: (a) contacting the immunogenic suspension or solution with a stabilizer of the invention, thereby forming a stabilized immunogenic suspension or solution; (b) cooling, at atmospheric pressure, the stabilized immunogenic suspension or solution to a temperature less than about the T'g value of the stabilized immunogenic suspension or solution; (c) drying the stabilized immunogenic suspension or solution (i.e., the primary desiccation or sublimation step) by sublimation of ice at low pressure; and (d) removing excess residual water (i.e., secondary drying or desorption step) by further reducing pressure and increasing the temperature of the stabilized immunogenic suspension or solution.

The cooling step (b) can occur at temperatures of less than about −40° C. (water freezing step). Drying the stabilized immunogenic suspensions or solution by sublimation of ice at low pressure (c) can occur at, for example, pressure lower than or equal to about 200 μbar, whereas a further reduction in pressure can occur at pressures lower than or equal to about 100 μbar. Finally, the temperature of the stabilized immunogenic suspension or solution during the removal of excess residual water (d) occurs at, for example, temperatures between about 20° C. and about 30° C.

The process of freeze-drying can also be performed with an immunogenic suspension or solution comprising live attenuated canine paramyxovirus and at least one active immunogenic component derived from a pathogen other than a paramyxovirus, which is mixed with a stabilizer according to the invention to obtain a freeze-dried stabilized multivalent immunogenic or vaccine composition.

The moisture content of the freeze-dried material can range from about 0.5% to about 5% w/w, preferably from about 0.5% to about 3% w/w, and more preferably from about 1.0% to about 2.6% w/w.

Advantageously, the stabilized immunogenic suspension or solution comprising at least one bulking agent has a high T'g value of between about −36° C. to about −30° C. A high T'g value allows for higher temperatures during the water freezing step of the freezing process and/or the freeze-drying process, thereby decreasing exposure of the live attenuated virus and the active immunogenic component to stress, avoiding substantial loss of activity.

Each step, including water freezing, and its removal during the primary and secondary desiccation, subjects the biological ingredients, such as pathogens, in the immunogenic suspensions or solutions of the invention to mechanical, physical and biochemical shock, which have potentially adverse effects upon the structure, appearance, stability, immunogenicity, infectivity and viability of the pathogens or biological ingredients.

The stabilizers of the invention allow good stability of live attenuated pathogens like canine paramyxovirus, and maintains the infectivity of, in particular, CDV and cPi2 during the freeze-drying process and during storage. The stability can be calculated by the difference between the infectivity titer before the freeze-drying step, and the infectivity titer after 12 months of storage of the freeze-dried stabilized immunogenic composition or vaccine composition at 4° C. Good stability can advantageously comprise a difference of only 1.2 $\log_{10}$, and preferably of only 1.0 $\log_{10}$. Methods for determining the infectivity titer are well known by those skilled in the art. Some methods for determining the infectivity titer are described in the Examples herein. Also, the stability can be estimated by fitting the $\log_{10}$ titer and the time points of the titration during the period of storage using linear regression calculations and/or algorithms.

Figure 1B:
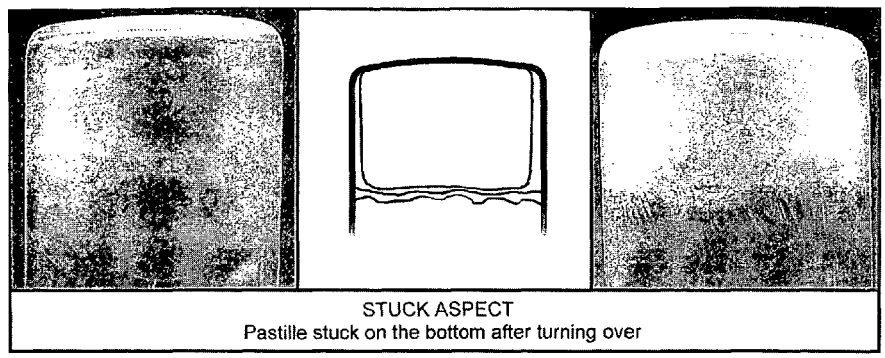
FIG. 1B shows photographs of a stuck aspect, a spooled aspect, and a de-duplicated aspect.
Figure 1B:
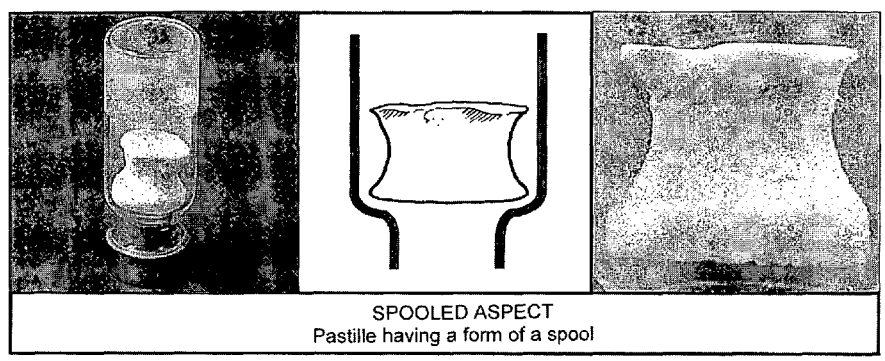
Figure 1B:
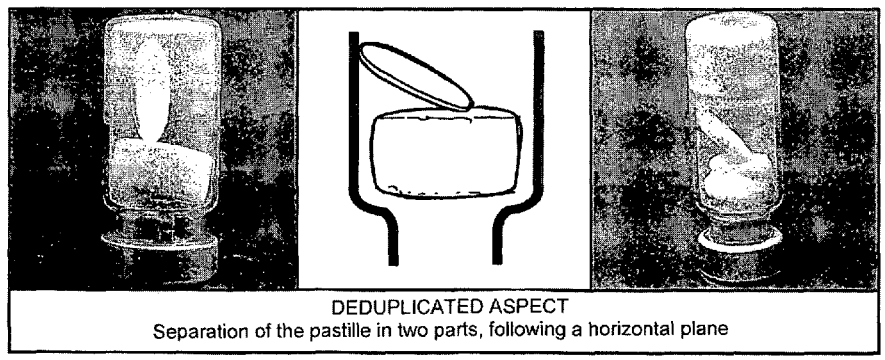

Further, the stabilizers of the invention allow for freeze-dried pastilles having a good aspect, in other words, having regular form and uniform color. An irregular form can be characterized by the presence of all or a part of the pastille stuck to the bottom of the recipient and remaining immobile after turning over and shearing (stuck aspect). Also, a pastille having a form of a spool (spooled aspect), or separation of the pastille in two parts, following a horizontal plane (de-duplicated aspect), or a pastille having an aspect of a mousse with irregular holes (spongy aspect), or a pastille having the aspect of foam into the recipient (meringue aspect) have an irregular form and are not accepted (FIGS. 1A and 1B).

The stabilized freeze-dried immunogenic compositions or vaccine compositions using a stabilizer according to the present invention and obtained by the process of freeze-drying described above are encompassed in the present invention.

In one embodiment, the freeze-dried stabilized live attenuated immunogenic or vaccine composition or the freeze-dried stabilized multivalent immunogenic composition or vaccine composition comprises: (i) a final concentration from about 20% to about 50% w/w of at least one reducing monosaccharide, and (ii) a final concentration from about 1.5% to about 6% w/w of at least one acid antioxidant.

In another embodiment, the freeze-dried stabilized live attenuated immunogenic or vaccine composition or the freeze-dried stabilized multivalent immunogenic or vaccine composition comprises: (i) a final concentration from about 20% to about 50% w/w of at least one reducing monosaccharide, (ii) a final concentration from about 1.5% to about 6% w/w of at least one acid antioxidant, and (iii) a final concentration from about 15% to about 70% w/w of at least one bulking agent.

The stabilized freeze-dried immunogenic compositions or vaccine compositions according to the present invention can be stored in a dry atmosphere at refrigerator temperatures and at room temperature, in particular at temperatures from about 2° C. to about 35° C., and more particularly from about 4° C. to about 25° C.

A further aspect of the present invention provides a kit comprising a first vial containing the freeze-dried stabilized live attenuated immunogenic composition or vaccine composition or the freeze-dried stabilized multivalent immunogenic composition or vaccine composition of the invention, and a second vial containing a solvent.

For its use and administration into a subject, the freeze-dried stabilized immunogenic composition or vaccine composition can be reconstituted by rehydration with a solvent. The solvent is typically water, such as demineralized or distilled water, water-for-injection, but can also comprise physiological solutions or buffers, such as for example phosphate buffer solution (PBS), or adjuvants including, but not limited to, water-in-oil emulsions, *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N, N-dioctadecyl-N',N'-bis(2-hydroxyethyl)-propanediamine), paraffin oil, muramyl dipeptide and the like. Other specific examples of adjuvants and adjuvant compositions are detailed herein.

Suitable adjuvants include fMLP (N-formyl-methionyl-leucyl-phenylalanine; U.S. Pat. No. 6,017,537) and/or acrylic acid or methacrylic acid polymer and/or a copolymer of maleic anhydride and of alkenyl derivative. The acrylic acid or methacrylic acid polymers can be cross-linked, e.g., with polyalkenyl ethers of sugars or of polyalcohols. These compounds are known under the term "carbomer" (*Pharmeuropa*, Vol. 8, No. 2, June 1996). A person skilled in the art may also refer to U.S. Pat. No. 2,909,462 (incorporated by reference), which discusses such acrylic polymers cross-linked with a polyhydroxylated compound containing at least 3 hydroxyl groups; a polyhydroxylated compound contains not more than 8 hydroxyl groups; as another example, the hydrogen atoms of at least 3 hydroxyls are replaced with unsaturated aliphatic radicals containing at least 2 carbon atoms. Radicals can contain from about 2 to about 4 carbon atoms, e.g., vinyls, allyls and other ethylenically unsaturated groups. The unsaturated radicals can themselves contain other substituents, such as methyl. The products sold under the name Carbopol® (Noveon Inc., Ohio, USA) are particularly suitable for use as adjuvants. They are cross-linked with an allyl sucrose or with allylpentaerythritol, as to which, mention is made of the products Carbopol® 974P, 934P, and 971P.

As to the copolymers of maleic anhydride and of alkenyl derivative, mention is made of the EMA® products (Monsanto), which are copolymers of maleic anhydride and of ethylene, which may be linear or cross-linked, for example, cross-linked with divinyl ether. Also, reference may be made to U.S. Pat. No. 6,713,068 and Regelson, W. et al., 1960; (incorporated by reference).

Cationic lipids containing a quaternary ammonium salt are described in U.S. Pat. No. 6,713,068, the contents of which are incorporated by reference, can also be used in the methods and compositions of the present invention. Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidylethanolamine; Behr J. P. et al, 1994), to form DMRIE-DOPE.

The total content of components in reconstituted ready-to-inject immunogenic compositions or vaccine compositions of the invention can be used to provide an injection at an isotonic concentration, e.g., within the range of about 100-600 mOsm, generally within about 250-450 mOsm, and preferably about 330 mOsm.

Dosages of live attenuated pathogens, notably CDV and cPi2, in a freeze-dried stabilized immunogenic compositions or vaccine composition, or in reconstituted ready-to-inject immunogenic compositions or vaccine compositions, can range from about $10^2$ to about $10^7$ $CCID_{50}$/dose. For proteins, polypeptides or glycoproteins in a freeze-dried stabilized multivalent immunogenic composition or vaccine composition, or in the reconstituted ready-to-use multivalent immunogenic compositions or vaccine compositions, can range in an equivalent titer before inactivation from about $10^5$ to about $10^9$ $CCID_{50}$ per dose, preferably from about $10^6$ to about $10^8$ $CCID_{50}$ per dose.

The reconstituted ready-to-use immunogenic compositions or vaccine compositions can be administered town animal by injection through the parenteral or mucosal route, preferably intramuscular and subcutaneous. However, administration of such reconstituted ready-to-use immunogenic compositions or vaccine compositions can also comprise intranasal, epicutaneous, topical, or oral administration. The volume of a dose for injection can be from about 0.1 ml to about 2.0 ml, and preferably about 1.0 ml.

The invention will now be further described by way of the following non-limiting Examples, given by way of illustration of various embodiments of the invention and are not meant to limit the present invention in any fashion.

EXAMPLES

Example 1

Preparation of Stabilizers

The compositions and the quantities of components into the stabilizers are shown in Table 1. "Dextran" comprises dextran-40,000 having a molecular weight of 40,000 Da.

TABLE 1

Compositions of the stabilizers

| Stabilizers | Reducing monosaccharide(s) or mixture | Acid antioxidant | Bulking Agent | Solvent |
|---|---|---|---|---|
| F2 | Glucose (5% w/v) Raffinose (5% w/v) | aspartic acid (0.50% w/v) | Dextran (10% w/v) | Water for injection (q.s. 100% v/v) |
| F2B | Glucose (3% w/v) Raffinose (3% w/v) | aspartic acid (0.20% w/v) | Dextran (6% w/v) | Water for injection (q.s. 100% v/v) |
| F6B | Galactose (3% w/v) Mannitol (6% w/v) | aspartic acid (0.40% w/v) | — | Water for injection (q.s. 100% v/v) |
| F33 | Glucose (5% w/v) Fructose (5% w/v) | aspartic acid (0.50% w/v) | Dextran (10% w/v) | Water for injection (q.s. 100% v/v) |
| F37 | Glucose (5% w/v) Raffinose (5% w/v) Sorbitol (10% w/v) | aspartic acid (0.50% w/v) | — | Water for injection (q.s. 100% v/v) |
| A | Glucose (1% w/v) Galactose (5% w/v) | aspartic acid (0.50% w/v) | Dextran (6% w/v) | Water for injection (q.s. 100% v/v) |
| H | Glucose (5% w/v) Raffinose (5% w/v) | aspartic acid (0.50% w/v) | Dextran (6% w/v) | Water for injection (q.s. 100% v/v) |
| K | Glucose (5% w/v) Sucrose (1% w/v) | aspartic acid (0.50% w/v) | Dextran (6% w/v) | Water for injection (q.s. 100% v/v) |
| U | Glucose (1% w/v) Galactose (1% w/v) | aspartic acid (0.50% w/v) | Dextran (6% w/v) | Water for injection (q.s. 100% v/v) |

For each stabilizer, one liter of distilled water was heated to a temperature of about 55° C. under agitation. The compounds were then added slowly to the hot water while remaining under agitation by a magnetic bar, to facilitate their dissolving. The agitation was maintained for about 30 minutes after the last addition, thereby resulting in a homogenous solution.

The solution was then cooled to room temperature. After the cooling of the solution, the stabilizer was sterilized by sterile filtration through a filter having a pore size cutoff of 0.22 μm (Optiscale Durapore). Sterile solutions of stabilizers F2, F2B, F6B, F33, F37, A, H, K and U were then stored at room temperature.

Example 2

Freeze-Drying Process

Each of the stabilizers obtained in Example 1 were used to stabilize a viral suspension. Four volumes of stabilizer were added at room temperature and under agitation to 6 volumes of a mixture of four live attenuated canine viruses. The live attenuated canine viruses were canine parainfluenza virus type 2 (cPi2), canine distemper virus (CDV), canine adenovirus type 2 (CAV2), and canine parvovirus (CPV).

The T'g values of these stabilized suspensions were measured with a differential scanning calorimeter (Mettler Toledo; Viroflay, France) and are shown in the Table 2.

TABLE 2

T'g value of stabilized suspensions

| Stabilizer | T'g value (° C.) | Stabilizer | T'g value (° C.) |
|---|---|---|---|
| F2 | −30.8 | A | −36.2 |
| F2B | −33.0 | H | −34.9 |
| F6B | −46.8 | K | −36.2 |
| F33 | −34.2 | U | −33.0 |
| F37 | −42.9 | — | — |

The stabilized suspensions formulated with the stabilizer were further freeze-dried. The freeze-drying cycle comprised 3 stages:

(1) Freezing stage: the stabilized suspensions, pooled in small bottles, were placed into a freeze-dryer and cooled by contact with the shelves at atmospheric pressure until they were completely frozen. The temperature of the shelves was lower than or equal to about −50° C.

(2) Sublimation stage (or primary desiccation): The pressure in the freeze-dryer was adjusted to a sufficiently low pressure to obtain sublimation of the ice (pressure lower than or equal to 120 μbar). The temperature was regulated such that no thawing during sublimation occurred, at a product temperature that was lower than or equal to −22° C.). Steam resulting from sublimation was frozen into the ice condenser located before the vacuum pumps.

(3) Desorption stage (or secondary desiccation): At the end of sublimation, when all of the ice disappeared from the product to be freeze-dried, the excess of free and/or bound residual water was eliminated by further reducing the pressure again to lower than or equal to 30 μbar in the freeze-dryer and by increasing the temperature to about 30° C.

After freeze-drying, the vacuum was broken using sterile nitrogen. Bottles were then closed, and the freeze-dryer was unloaded. The moisture content of each stabilized freeze-dried vaccine was measured and shown in Table 3.

TABLE 3

Moisture content of stabilized freeze-dried vaccines

| Stabilizer | Moisture Content (%) | Stabilizer | Moisture Content (%) |
|---|---|---|---|
| F2 | 1.32 | A | 2.01 |
| F2B | 2.16 | H | 2.60 |
| F6B | 3.63 | K | 2.58 |
| F33 | 2.03 | U | 1.08 |
| F37 | 3.27 | — | — |

Example 3

Stability Studies after Freeze-Drying

The freeze-dried pastilles obtained after the freeze-drying of the stabilized suspensions as described in Example 2 were observed to distinguish between abnormal pastilles and those having a regular form. The freeze-dried pastilles containing a stabilizer of the present invention and further comprising a bulking agent (i.e. F2, F2B, F33, A, H, K and U) have a good aspect; with only 5 pastilles with F2 stabilizer having a stuck aspect over 110 (4.5%). The freeze-dried stabilized vaccines were then stored at +4° C.

Determination of viral titer of the freeze-dried vaccines was performed by the calculation of the mean titer of three titrations repeated on the same vaccine. The freeze-dried vaccines obtained after the freeze-drying as described in Example 2 were rehydrated in 1 ml of water for injection. Each vaccine was subsequently diluted to obtain dilutions from $-3.8$ $\log_{10}$ to $-6.8$ $\log_{10}$.

For cPi2 titration, each dilution was deposited 6 times on a titration plate in an amount of 50 µl per well, with 50 µl of a solution of anti-hepatitis antibodies and 150 µl of a cellular suspension of Madin-Darby Canine Kidney cells (MDCK cells) at 100,000 cells/ml. The MDCK cells were cultured in F15 culture medium supplemented with 2% fetal calf serum. As a control, 100 µl of the dilution and 150 µl of MDCK cells were deposited in the same well. All titration plaques were kept at 37° C. for 7 days. After incubation, the supernatants were removed from each well of the titration plates and placed into new titration plates with conic wells. Guinea pig erythrocytes (Alsever sp.) were added to each well containing the supernatant. The dilution of erythrocyte solution was the same in all of the wells. After 3-4 hours at +4° C., the results were obtained by placing the plates on white paper. Viral attacks were then detected by the presence of an easily identifiable pellet.

For CDV titration, each dilution was deposited 6 times on a titration plate, in an amount of 50 µl per well, with 50 µl of a solution of anti-cPi2 antibodies and 150 µl of a cellular suspension of VERO cells (monkey kidney cells) at 120,000 cells/ml. Vero cells were cultured in Eagle's minimal essential medium (MEM culture medium) supplemented with 2% fetal calf serum. As a control, one hundred µl of the dilution and 150 µl of VERO cells were deposited in the same well. All titration plaques were kept at 37° C. for 7 days. After incubation, the titration plates were placed under a microscope. Viral attacks were detected by the degradation of the VERO cells. The viral titers were expressed in $\log_{10}$ of 50% cell culture infective dose per milliliter ($CCID_{50}$/ml).

Table 4 shows the decrease of cPi2 and CDV titers, expressed in $\log_{10}$ $CCID_{50}$/ml, after freeze-drying step and a storage period of 12 months at 4° C.

TABLE 4

| Decrease of cPi2 and CDV titers after freeze-drying and 12-month storage at 4° C. | | |
|---|---|---|
| Stabilizer | cPi2 titer decrease | CDV titer decrease |
| F2 | −0.36 | −0.60 |
| F2B | −0.43 | −1.06 |
| F6B | −0.93 | −0.56 |
| F33 | −0.81 | −0.15 |
| F37 | −1.06 | −0.91 |
| A | −0.69 | −0.69 |
| H | −0.51 | −0.64 |
| K | −0.73 | −1.00 |
| U | −0.50 | +0.15 |

The results show very good stability of both CDV and cPi2 viruses for a long storage period at 4° C. For some of these freeze-dried stabilized vaccines, titrations of CAV2 and CPV were performed in triplicate. The results of these titrations are given in the Table 5 as a decrease of the mean value obtained from the three titrations, expressed in $\log_{10}$ $CCID_{50}$/ml, just after the freeze-drying step and after a storage period of 3 months (T0+3) at 4° C.

TABLE 5

| Decrease of CAV2 and CPV titers after freeze-drying and 3-month storage at 4° C. | | |
|---|---|---|
| Stabilizer | CAV2 titer decrease | CPV titer decrease |
| A | −0.20 | −0.10 |
| H | −0.47 | −0.20 |
| K | −0.36 | +0.10 |

The effects of various compounds of the stabilizer on the stability of CDV and cPi2 during and after freeze-drying step were studied. In particular, the effect of the non reducing oligosaccharide on the stability of CDV was checked. The results were given by statistical analysis in FIG. 2A and in Table 6.

TABLE 6

| Average titer and standard deviation at the end of the freeze-drying step (at T0) of CDV stabilized with a stabilizer comprising non reducing oligosaccharide (n = 72). | | | |
|---|---|---|---|
| Non-reducing oligosaccharide (% w/v final concentration) | Count | Average titer of CDV ($\log_{10}$ $CCID_{50}$/ml) | Standard Deviation |
| 0 | 18 | 4.78 | 0.20 |
| 0.5 | 27 | 4.69 | 0.25 |
| 2.5 | 27 | 4.76 | 0.34 |

The presence of non reducing oligosaccharide in the stabilizer has no effect on the CDV titer (ANOVA p-value=0.5142).

The effect of the reducing monosaccharide on the stability of CDV was checked. The results were subjected to statistical analysis and are shown in FIG. 2B and in Table 7.

TABLE 7

Average titer and standard deviation at the end of the freeze-drying step (at T0) of CDV stabilized with a stabilizer comprising a reducing monosaccharide (n = 72).

| Reducing monosaccharide (% w/v final concentration) | Count | Average titer of CDV ($\log_{10}$ CCID$_{50}$/ml) | Standard Deviation |
|---|---|---|---|
| 0.5 | 30 | 4.58 | 0.27 |
| 1 | 6 | 4.61 | 0.13 |
| 2.5 | 24 | 4.90 | 0.22 |
| 3 | 6 | 4.92 | 0.20 |
| 5 | 6 | 4.82 | 0.12 |

As shown in Table 7 and in FIG. 2B, the presence of reducing monosaccharide in the stabilizer has a positive effect on the CDV titer (ANOVA p=0.0000).

Figure 3:
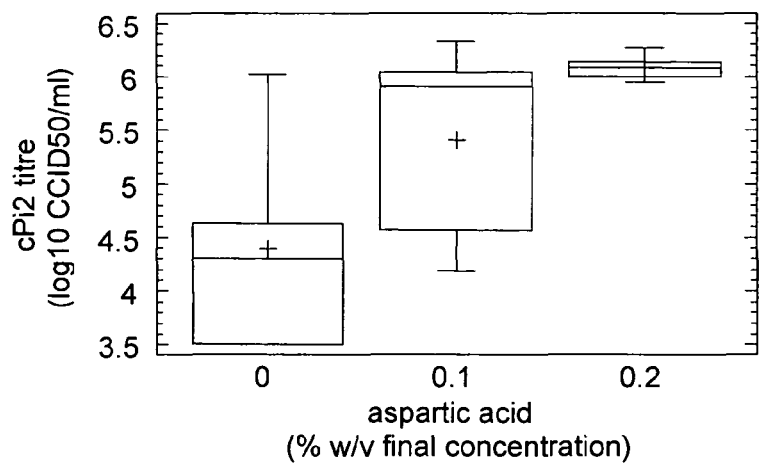
FIG. 3 depicts graphs demonstrating the effect of an antioxidant compound on cPi2 titer, expressed in $\log_{10}$ $CCID_{50}$/ml (A) at the end of the freeze-drying step (at T0), and (B) after a storage period of 3 months at +4° C. (T+3 months), wherein the final concentration is expressed in % weight/volume.
Figure 3:
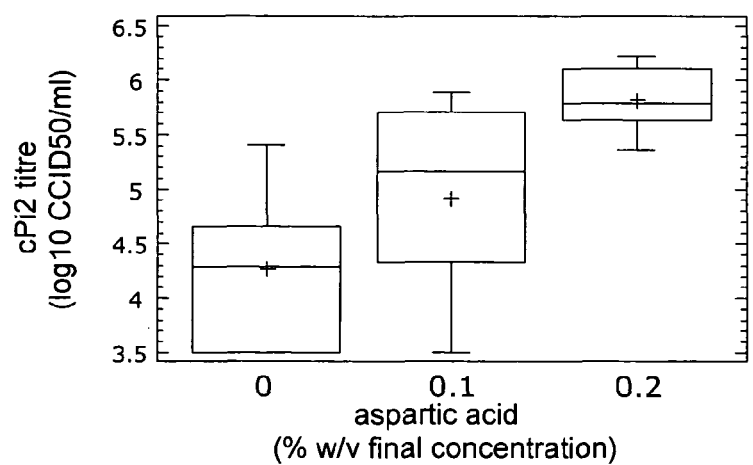

The effect of the antioxidant compound on the stability of cPi2 was also studied. The results were subjected to statistical analysis in FIGS. 3A and 3B, and in Tables 8 and 9.

TABLE 8

Average titer and standard deviation of cPi2 stabilized with a stabilizer with or without aspartic acid (n = 15), at the end of the freeze-drying step (at T0).

| Aspartic Acid (% w/v final concentration) | Count | Average titer of cPi2 ($\log_{10}$ CCID$_{50}$/ml) | Standard Deviation |
|---|---|---|---|
| 0 | 5 | 4.39 | 1.04 |
| 0.1 | 5 | 5.41 | 0.96 |
| 0.2 | 5 | 6.09 | 0.13 |

TABLE 9

Average titer and standard deviation of cPi2 stabilized with a stabilizer with or without aspartic acid (n = 15), after freeze-drying step and a 3-month storage period at 4° C. (at T0 + 3 months).

| Aspartic Acid (% w/v final concentration) | Count | Average titer of cPi2 ($\log_{10}$ CCID$_{50}$/ml) | Standard Deviation |
|---|---|---|---|
| 0 | 5 | 4.27 | 0.81 |
| 0.1 | 5 | 4.92 | 1.00 |
| 0.2 | 5 | 5.82 | 0.35 |

The presence of antioxidant compound in the stabilizer has been found to have a positive effect on the cPi2 titer (ANOVA p=0.0000) during the freeze-drying step and during the storage period.

Example 4

Comparative Studies of the Stabilizer Components

The F2 stabilizer (Example 1) was used as a reference to measure the decline in titer of the freeze-dried vaccines in comparison to other stabilized freeze-dried formulations. These formulations were obtained by modification of each component as shown in Table 10.

Stabilizer F63 is identical to F2, but lacks the antioxidant compound.

Stabilizer F62 is identical to F2, but includes phenylalanine instead of aspartic acid.

Stabilizer F42 is identical to F2, but includes aspartic acid monosodium salt instead of aspartic acid.

Stabilizer F32 is identical to F2, but includes betaine instead of a reducing monosaccharide.

TABLE 10

Compositions of the formulations

| Stabilizer | Mixture containing reducing monosaccharide or variant | Acid antioxidant or variant | Bulking agent | Solvent |
|---|---|---|---|---|
| F63 | Glucose (5% w/v) Raffinose (5% w/v) | — | Dextran (10% w/v) | Water for injection (q.s. 100% v/v) |
| F62 | Glucose (5% w/v) Raffinose (5% w/v) | Phenylalanine (0.50% w/v) | Dextran (10% w/v) | Water for injection (q.s. 100% v/v) |
| F42 | Glucose (5% w/v) Raffinose (5% w/v) | Aspartic acid monosodium salt (0.50% w/v) | Dextran (10% w/v) | Water for injection (q.s. 100% v/v) |
| F32 | Betaine (5% w/v) Raffinose (5% w/v) | Aspartic acid (0.50% w/v) | Dextran (10% w/v) | Water for injection (q.s. 100% v/v) |

These formulations have been used to stabilize the vaccines of Example 2 and were freeze-dried according to the process described herein. The freeze-dried vaccines were rehydrated in 1 ml of water for injection. The determination of the cPi2 titer and the CDV titer of vaccines were performed by calculation of the mean titer of three titrations repeated on the same vaccine as done in Example 3. The titers were measured after the freeze-drying process for each formulation. These titers, expressed in $\log_{10}$ CCID$_{50}$/ml, are given in the Table 11.

TABLE 11

Decrease of titers during freeze-drying step of freeze-dried/rehydrated vaccines stabilized with various formulations.

| Stabilizer | cPi2 titer | CDV titer |
|---|---|---|
| F63 | −2.22 | −0.46 |
| F62 | −2.42 | −0.74 |
| F32 | −3.29 | −1.86 |
| F42 | −1.12 | −0.83 |
| F42 after 12 month storage at 4° C. | −1.60 | −1.98 |

These results show that absence of antioxidant compound yields a significant loss in titer for cPi2. Inclusion of the amino acid phenylalanine, which lacks any antioxidant effect, also results in a loss in titer for both cPi2 and CDV. Similarly, inclusion of the monosodium salt of the antioxidant aspartic acid yields a loss in titer for both cPi2 and CDV. These results also demonstrate that an absence of reducing monosaccharide results in a high loss in titer for cPi2 as well as for CDV.

Example 5

Safety Evaluation of Stabilized Vaccines in Dogs

Some of the freeze-dried vaccines described in Example 2 were administered to dogs after rehydration in sterile injectable water. The vaccines contained the A, H, K and F2B stabilizers described in Example 1.

Four specific pathogen-free (SPF) dogs aged 3 to 5 months old and 4 conventional dogs aged 3 to 5 months old, were randomly allocated into 4 groups of two animals, wherein each group had one SPF dog and one conventional dog. For each group, two dogs were immunized subcutaneously on day 0 with a double dose (2 ml) of their corresponding stabilized vaccine. On day 14, dogs were immunized subcutaneously with a single dose (1 ml) of the same stabilized vaccine.

Immediate local reactions and immediate general reactions, rectal temperatures, local reactions, general reactions and clinical symptoms have been observed. No local or general reaction following administration was observed. Therefore, the safety of the stabilized vaccines appears to be high.

Having thus described in detail preferred embodiments of the present invention, it is to be understood that the invention defined by the appended claims is not to be limited by particular details set forth in the above description as many apparent variations thereof are possible without departing from the spirit or scope thereof.

The invention will be further described by the following numbered paragraphs:

1. A stabilizer for a freeze-dried live attenuated canine distemper (CDV) and canine paramyxovirus type 2 (cPi2) immunogenic composition comprising at least one reducing monosaccharide and at least one acid antioxidant compound, wherein the at least one acid antioxidant compound comprises aspartic acid, glutamic acid, ascorbic acid, or combinations thereof.
2. The stabilizer of paragraph 1, wherein the at least one reducing monosaccharide comprises glucose, galactose, fructose, mannose, sorbose, or combinations thereof.
3. The stabilizer of paragraph 1 or 2, further comprising at least one bulking agent.
4. The stabilizer of paragraph 3, wherein the at least one bulking agent comprises dextran, maltodextrin, polyvinylpyrrolidone, hydroxyethyl starch, or combinations thereof.
5. The stabilizer of any one of paragraphs 1 to 4, further comprising at least one sugar alcohol.
6. The stabilizer of paragraph 5, wherein the at least one sugar alcohol comprises sorbitol, mannitol xylitol, maltitol or combinations thereof.
7. The stabilizer of any one of paragraphs 1 to 6, further comprising at least one non-reducing oligosaccharide.
8. The stabilizer of paragraph 7, wherein the at least one non-reducing oligosaccharide comprises trehalose, sucrose, raffinose or combinations thereof.
9. The stabilizer of any one of paragraphs 1 to 8, further comprising at least one sugar alcohol and at least one non-reducing oligosaccharide.
10. The stabilizer of paragraph 9, wherein the at least one sugar alcohol comprises sorbitol, mannitol xylitol, maltitol or combinations thereof, and wherein the at least one non-reducing oligosaccharide comprises trehalose, sucrose, raffinose or combinations thereof.
11. An immunogenic suspension or solution comprising live attenuated paramyxovirus comprising CDV and cPi2, mixed with the stabilizer of any one of paragraphs 1 to 10.
12. The immunogenic suspension or solution of paragraph 11, wherein the immunogenic suspension or solution is a multivalent immunogenic suspension or solution that further comprises at least one active immunogenic component derived from a pathogen other than paramyxovirus.
13. The immunogenic suspension or solution of paragraph 12, wherein the at least one active immunogenic component is derived from a pathogen comprising Adenoviridae, Parvoviridae, Coronaviridae, Herpesviridae, Poxyirididae, Rhabdoviridae, or combinations thereof.
14. The immunogenic suspension or solution of paragraphs 12 or 13, wherein the at least one active immunogenic component comprises live attenuated canine adenovirus type 2 (CAV2) and live attenuated canine parvovirus (CPV).
15. The immunogenic suspension or solution of any one of paragraphs 12 to 14, wherein the at least one active immunogenic component comprises a viral vector comprising one or more heterologous immunogens.
16. The immunogenic suspension or solution of any one of paragraphs 12 to 15, wherein the at least one active immunogenic component comprises a plasmid vector comprising one or more heterologous immunogens.
17. The immunogenic suspension or solution of any one of paragraphs 11 to 16, wherein the stabilizer comprises at least one reducing monosaccharide at a final concentration from about 1% to about 5% w/v.
18. The immunogenic suspension or solution of any one of paragraphs 11 to 16, wherein the stabilizer comprises at least one reducing monosaccharide at a final concentration from about 1.5% to about 5% w/v.
19. The immunogenic suspension or solution of any one of paragraphs 11 to 16, wherein the stabilizer comprises at least one reducing monosaccharide at a final concentration from about 1.5% to about 4% w/v.
20. The immunogenic suspension or solution of any one of paragraphs 11 to 16, wherein the stabilizer comprises at least one reducing monosaccharide at a final concentration from about 2.5% to about 3% w/v.
21. The immunogenic suspension or solution of any one of paragraphs 11 to 20, wherein the stabilizer comprises at least one acid antioxidant compound at a final concentration from about 0.1% to about 0.3% w/v.
22. The immunogenic suspension or solution of any one of paragraphs 11 to 20, wherein the stabilizer comprises at least one acid antioxidant compound at a final concentration from about 0.1% to about 0.25% w/v.
23. The immunogenic suspension or solution of any one of paragraphs 11 to 20, wherein the stabilizer comprises at least one acid antioxidant compound at a final concentration of about 0.2% w/v.
24. The immunogenic suspension or solution of any one of paragraphs 11 to 23, wherein the stabilizer comprises at least one bulking agent at a final concentration from about 0.5% to about 7.5% w/v.
25. The immunogenic suspension or solution of any one of paragraphs 11 to 24, the stabilizer comprises at least one bulking agent at a final concentration from about 1.5% to about 5% w/v.

26. The immunogenic suspension or solution of paragraph 11, wherein the stabilizer comprises at least one sugar alcohol at a final concentration from about 0.5% to about 5% w/v and at least one reducing monosaccharide, with the proviso that the final concentration of the at least one reducing monosaccharide and the at least one sugar alcohol is equal to or less than about 7.5% w/v.

27. The immunogenic suspension or solution of paragraph 11, wherein the stabilizer comprises at least one non-reducing oligosaccharide from about 0.5% to about 5% w/v final concentration and at least one reducing monosaccharide, with the proviso that the final concentration of the reducing monosaccharide and the non-reducing oligosaccharide is equal to or less than about 7.5% w/v.

28. The immunogenic suspension or solution of paragraph 11, wherein the stabilizer comprises at least one sugar alcohol at a final concentration from about 0.5% to about 5% w/v, at least one non-reducing oligosaccharide at a final concentration from about 0.5% to about 5% w/v, and at least one reducing monosaccharide, with the proviso that the final concentration of reducing monosaccharide, sugar alcohol and non-reducing oligosaccharide is equal to or less than about 12.5% w/v.

29. The immunogenic suspension or solution of paragraph 11, wherein the stabilizer comprises: (i) a final concentration of about 1% to about 5% w/v of a mixture of two reducing monosaccharides, (ii) a final concentration of about 0.1% to about 0.3% w/v of at least one acid antioxidant, and (iii) a final concentration of about 0.5% to about 7.5% w/v of at least one bulking agent.

30. The immunogenic suspension or solution of paragraph 11, wherein the stabilizer comprises: (i) a final concentration from about 1% to about 5% w/v of at least one reducing monosaccharide, (ii) a final concentration from about 0.5% to about 5% w/v of at least one non-reducing oligosaccharide, (iii) a final concentration from about 0.1% to about 0.3% w/v of at least one acid antioxidant, and (iv) a final concentration from about 0.5% to about 7.5% w/v of at least one bulking agent, with the proviso that the final concentration of (i) and (ii) is equal to or less than about 7.5% w/v.

31. The immunogenic suspension or solution of paragraph 11, wherein the stabilizer comprises: (i) a final concentration from about 1.5% to about 4% w/v of at least one reducing monosaccharide, (ii) a final concentration from about 0.5% to about 2.5% w/v of at least one non-reducing oligosaccharide, (iii) a final concentration from about 0.1% to about 0.25% w/v of at least one acid antioxidant, and (iv) a final concentration from about 1.5% to about 5% w/v of at least one bulking agent, with the proviso that the final concentration of (i) and (ii) is equal to or less than about 5% w/v.

32. The immunogenic suspension or solution of paragraph 11, wherein the stabilizer comprises: (i) a final concentration from about 1% to about 5% w/v of at least one reducing monosaccharide, (ii) a final concentration from about 0.5% to about 5% w/v of at least one sugar alcohol, (iii) a final concentration from about 0.1% to about 0.3% w/v of at least one acid antioxidant, with the proviso that the final concentration of (i) and (ii) is equal to or less than about 7.5% w/v.

33. The immunogenic suspension or solution of paragraph 11, wherein the stabilizer comprises: (i) a final concentration from about 1.5% to about 4% w/v of at least one reducing monosaccharide, (ii) a final concentration from about 1.5% to about 3% w/v of at least one sugar alcohol, and (iii) a final concentration from about 0.1% to about 0.25% w/v of at least one acid antioxidant, with the proviso that the final concentration of (i) and (ii) is equal to or less than about 5% w/v.

34. The immunogenic suspension or solution of paragraph 11, wherein the stabilizer comprises: (i) a final concentration from about 1% to about 5% w/v of at least one reducing monosaccharide, (ii) a final concentration from about 0.5% to about 5% w/v of at least one sugar alcohol, (iii) a final concentration from about 0.5% to about 5% w/v of at least one non-reducing oligosaccharide, and (iv) a final concentration from about 0.1% to about 0.3% w/v of at least one acid antioxidant, with the proviso that the final concentration of (i), (ii) and (iii) is equal to or less than about 12.5% w/v.

35. The immunogenic suspension or solution of paragraph 11, wherein the stabilizer comprises: (i) a final concentration from about 1.5% to about 4% w/v of at least one reducing monosaccharide, (ii) a final concentration from about 0.5% to about 5% w/v of at least one sugar alcohol, (iii) a final concentration from about 0.5% to about 2.5% w/v of at least one non-reducing oligosaccharide, and (iv) a final concentration from about 0.1% to about 0.25% w/v of at least one acid antioxidant, with the proviso that the final concentration of (i), (ii) and (iii) is equal to or less than about 10% w/v.

36. A process for freeze-drying a live attenuated CDV and cPi2 immunogenic suspension or solution of any one of paragraphs 11 to 35, comprising (a) contacting the suspension or solution with the stabilizer, thereby forming a stabilized immunogenic suspension or solution; (b) cooling, at atmospheric pressure, the stabilized immunogenic suspension or solution to a temperature of less than about the T'g value of the stabilized immunogenic suspension or solution; (c) drying the stabilized immunogenic suspension or solution by sublimation of ice at low pressure; and (d) removing excess residual water by further reducing pressure and increasing the temperature of the stabilized immunogenic suspension or solution.
37. The process of paragraph 36, wherein the temperature in step (b) is less than about −40° C.
38. The process of paragraph 36 or 37, wherein the pressure in step (c) is less than or equal to about 200 μbar.
39. The process of paragraph 36 or 37, wherein the pressure in step (d) is less than or equal to about 100 μbar.
40. The process of any one of paragraphs 36 to 39, wherein the temperature in step (d) is between about 20° C. and about 30° C.
41. The process of any one of paragraphs 36 to 40, further comprising at least one active immunogenic component derived from a pathogen other than paramyxovirus.
42. The process of paragraph 41, wherein the at least one active immunogenic component is derived from a pathogen comprising Adenoviridae, Parvoviridae, Coronaviridae, Herpesviridae, Poxyiridae, Rhabdoviridae, or combinations thereof.
43. The process of paragraph 41 or 42, wherein the at least one immunogenic component comprises live attenuated canine adenovirus type 2 (CAV2) and live attenuated canine parvovirus (CPV).
44. The process of any one of paragraphs 41 to 43, wherein the at least one immunogenic component comprises a viral vector comprising one or more heterologous immunogens.

45. The process of any one of paragraphs 41 to 44, wherein the at least one immunogenic component comprises a plasmid vector comprising one or more heterologous immunogens.
46. A freeze-dried stabilized live attenuated CDV and cPi2 immunogenic composition produced by the process of any one of paragraphs 36 to 45.
47. A freeze-dried stabilized live attenuated CDV and cPi2 immunogenic composition, comprising: (i) a final concentration from about 20% to about 50% w/w of at least one reducing monosaccharide, (ii) a final concentration from about 1.5% to about 6% w/w of at least one acid antioxidant comprising aspartic acid, glutamic acid, ascorbic acid, or combinations thereof.
48. A freeze-dried stabilized live attenuated CDV and cPi2 immunogenic composition, comprising: (i) a final concentration from about 20% to about 50% w/w of at least one reducing monosaccharide, (ii) a final concentration from about 2% to about 6% w/w of at least one acid antioxidant comprising aspartic acid, glutamic acid, ascorbic acid, or combinations thereof, and (iii) a final concentration from about 15% to about 70% w/w of at least one bulking agent.
49. A freeze-dried stabilized multivalent immunogenic composition comprising live attenuated CDV, live attenuated cPi2, and at least one active immunogenic component derived from a pathogen other than paramyxovirus, and comprising: (i) a final concentration from about 20% to about 50% w/w of at least one reducing monosaccharide, (ii) a final concentration from about 1.5% to about 6% w/w of at least one acid antioxidant comprising aspartic acid, glutamic acid, ascorbic acid, or combinations thereof.
50. The multivalent immunogenic composition of paragraph 49 or 50, wherein the at least one active immunogenic component is derived from a pathogen comprising Adenoviridae, Parvoviridae, Coronaviridae, Herpesviridae, Poxyiridae, Rhabdoviridae, or combinations thereof.
51. The multivalent immunogenic composition of paragraph 49, wherein the at least one immunogenic component comprises live attenuated canine adenovirus type 2 (CAV2) and live attenuated canine parvovirus (CPV).
52. The multivalent immunogenic composition of any one of paragraphs 49 to 51, wherein the at least one immunogenic component comprises a viral vector comprising one or more heterologous immunogens.
53. The multivalent immunogenic composition of any one of paragraphs 41 to 52, wherein the at least one immunogenic component comprises a plasmid vector comprising one or more heterologous immunogens.
54. A freeze-dried stabilized multivalent immunogenic composition comprising live attenuated CDV, live attenuated cPi2 and at least one active immunogenic component derived from a pathogen other than paramyxovirus, and comprising: (i) a final concentration from about 20% to about 50% w/w of at least one reducing monosaccharide, (ii) a final concentration from about 2% to about 6% w/w of at least one acid antioxidant comprising aspartic acid, glutamic acid, ascorbic acid, or combinations thereof, and (iii) a final concentration from about 15% to about 70% w/w of at least one bulking agent.
55. The multivalent immunogenic composition of paragraph 54, wherein the at least one active immunogenic component is derived from a pathogen comprising Adenoviridae, Parvoviridae, Coronaviridae, Herpesviridae, Poxyiridae, Rhabdoviridae, or combinations thereof
56. The multivalent immunogenic composition of paragraph 54 or 55, wherein the at least one immunogenic component comprises live attenuated canine adenovirus type 2 (CAV2) and live attenuated canine parvovirus (CPV).
57. The multivalent immunogenic composition of any one of paragraphs 54 to 56, wherein the at least one immunogenic component comprises a viral vector comprising one or more heterologous immunogens.
58. The multivalent immunogenic composition of any one of paragraphs 54 to 57, wherein the at least one immunogenic component comprises a plasmid vector comprising one or more heterologous immunogens.
59. A kit comprising a first vial containing a freeze-dried stabilized immunogenic composition of any one of paragraphs 46 to 58, and a second vial containing a solvent.
60. The kit of paragraph 49, wherein the solvent is selected from the group consisting of demineralized water, distilled water, water-for-injection, buffer, and adjuvant.

The invention claimed is:

1. A stabilizer for a freeze-dried live attenuated canine distemper (CDV) and canine parainfluenza type 2 (cPi2) immunogenic composition comprising at least one reducing monosaccharide and at least one acid antioxidant compound, wherein the at least one acid antioxidant compound consists of aspartic acid; and wherein the at least one reducing monosaccharide consists of glucose, galactose, fructose, mannose, sorbose, or combinations thereof;
   wherein the at least one reducing monosaccharide is at a concentration from 20% to 50% w/w and the at least one acid antioxidant is at a concentration from 1.5% to 6% w/w; and wherein the stabilizer further consists of:
   (a) a bulking agent selected from dextran, maltodextrin, polyvinylpymolidone, hydroxyethyl starch, and combinations thereof, or
   (b) a sugar alcohol selected from sorbitol, mannitol, xylitol, maltitol and combinations thereof, or
   (c) a combination thereof; and
   wherein the stabilizer is capable of reducing the amount of CDV and cPi2 titer lost during the freezing process by at least 0.5 logs.
2. The stabilizer of claim 1 wherein the reducing monosaccharide consists of glucose, galactose, or glucose combined with any one of galactose, fructose, mannose, or sorbose.
3. The stabilizer of claim 2 wherein the bulking agent is dextran present in an amount from about 10% to about 70% w/w.
4. The stabilizer of claim 3 wherein no sugar alcohol is present.
5. The stabilizer of claim 4 wherein and the reducing monosaccharide consists of glucose.
6. The stabilizer of claim 5 further comprising a non-reducing oligosaccharide, which consists of either raffinose or sucrose.
7. The stabilizer of claim 2 wherein the at least one reducing monosaccharide is glucose.
8. The stabilizer of claim 7 wherein the sugar alcohol consists of mannitol, sorbitol, or a combination thereof.
9. A liquid immunogenic composition comprising live attenuated paramyxoviruses comprising CDV and cPi2, mixed with the stabilizer of claim 1.
10. The immunogenic composition of claim 9, which further comprises at least one active immunogenic component derived from a pathogen other than paramyxovirus.

11. The immunogenic composition of claim 10, wherein
(a) the at least one active immunogenic component is derived from a pathogen selected from Adenoviridae, Parvoviridae, Coronaviridae, Herpesviridae, Poxviridae, Rhabdoviridae, and combinations thereof; or
(b) the at least one active immunogenic component is selected from live attenuated canine adenovirus type 2 (CAV2), live attenuated canine parvovirus (CPV), and combinations thereof; or
(c) the at least one active immunogenic component is a viral vector comprising nucleotides encoding one or more heterologous, non-paramyxovirus immunogen(s); or
(d) the at least one active immunogenic component is a plasmid vector comprising nucleotides encoding one or more heterologous non-paramyxovirus immunogen(s).

12. The immunogenic composition of claim 9, wherein the stabilizer components are present in the following w/v amounts, relative to the final liquid composition, prior to freeze-drying:
(a) the reducing monosaccharide is present from about 1% to about 5% (w/v);
(b) the aspartic acid is present from about 0.1% to about 0.2.5% or about 0.5% to about 7.5% (w/v); and
(c) the bulking agent is present from about 1.5% to about 5% (w/v).

13. The immunogenic composition of claim 9, wherein the stabilizer components are present in the following w/v amounts, relative to the final liquid composition, prior to freeze-drying:
(a) the reducing monosaccharide is present from about 1.5% to about 4% w/v;
(b) the aspartic acid is present from about 0.5% to 7.5%; and
(c) the sugar alcohol is present from about 0.5% to 5.0%.

14. A freeze-dried stabilized live attenuated CDV and cPi2 immunogenic composition produced by freeze-drying the liquid composition of any one of claims 9 to 13.

* * * * *